US008119861B2

(12) United States Patent
Napier et al.

(10) Patent No.: US 8,119,861 B2
(45) Date of Patent: Feb. 21, 2012

(54) ELONGASE AND USES THEREOF

(75) Inventors: Johnathan A. Napier, Preston (GB); Olga Sayanova, St. Albans (GB); Monica Venegas Caleron, Harpenden (GB)

(73) Assignee: BASF Plant Science GmbH, Ludwigshafen (DE)

( * ) Notice: Subject to any disclaimer, the term of this patent is extended or adjusted under 35 U.S.C. 154(b) by 421 days.

(21) Appl. No.: 12/279,560

(22) PCT Filed: Feb. 13, 2007

(86) PCT No.: PCT/GB2007/000491
§ 371 (c)(1),
(2), (4) Date: Aug. 15, 2008

(87) PCT Pub. No.: WO2007/093776
PCT Pub. Date: Aug. 23, 2007

(65) Prior Publication Data
US 2009/0019559 A1    Jan. 15, 2009

(30) Foreign Application Priority Data
Feb. 16, 2006  (GB) .................................. 0603160.3

(51) Int. Cl.
| | |
|---|---|
| *A01H 5/00* | (2006.01) |
| *C12N 15/82* | (2006.01) |
| *C12N 1/20* | (2006.01) |
| *C12N 1/00* | (2006.01) |
| *C07H 21/04* | (2006.01) |

(52) U.S. Cl. ........ 800/298; 800/281; 435/410; 435/419; 435/252.3; 435/254.11; 536/23.2

(58) Field of Classification Search .......................... None
See application file for complete search history.

(56) References Cited

U.S. PATENT DOCUMENTS
2006/0246556 A1  11/2006  Napier et al.
2007/0224661 A1  9/2007  Cirpus et al.

FOREIGN PATENT DOCUMENTS
| | | | |
|---|---|---|---|
| WO | WO-95/15387 A2 | 6/1995 | |
| WO | WO-01/94565 A2 | 12/2001 | |
| WO | WO-2004/057001 A2 | 7/2004 | |
| WO | WO-2004/087879 A2 | 10/2004 | |
| WO | WO-2005/083053 A2 | 9/2005 | |
| WO | WO-2005/103253 A1 | 11/2005 | |
| WO | WO-2006/012325 A1 | 2/2006 | |
| WO | WO-2007/061742 A2 | 5/2007 | |

OTHER PUBLICATIONS

Broun et al, Science 282:1315-1317, Nov. 13, 1998.*
Van de Loo et al, PNAS, USA 92:6743-6747, Jul. 1995.*
Doerks et al, TIG 14(6): 248-250, Jun. 1998.*
Brenner, S.E., TIG 15(4): 132-133, Apr. 1999.*
Bork et al, TIG 12(10): 425-427, Oct. 1996.*
Leonard et al, Progress in Lipid Research 43: 36-54, 2004.*
Fourgoux-Nicol et al, Plant Mol Biol 40: 857-872, 1999.*
Chu, F.-L. E., et al., "Arachidonic Acid Synthetic Pathways of the Oyster Protozoan Parasite, *Perkinsus marinus*: Evidence for Usage of a Delta-8 Pathway", Molecular & Biochemical Parasitology, 2004, vol. 133, pp. 45-51.
Abbadi, A., et al., "Biosynthesis of Very-Long-Chain Polyunsaturated Fatty Acids in Transgenic Oilseed: Constraints on Their Accumulation", The Plant Cell, 2004, vol. 16, pp. 2734-2748.
Qi, B., et al., "Production of Very Long Chain Polyunsaturated Omega-3 and Omega-6 Fatty Acids in Plants", Nature Biotechnology, 2004, vol. 22, No. 6, pp. 739-745.
Venegas-Calerón, M., et al., "Co-Transcribed Genes for Long Chain Polyunsaturated Fatty Acid Biosynthesis in the Protozoon *Perkinsus marinus* Include a Plant-like FAE1 3-Ketoacyl Coenzyme a Synthase", Journal of Biological Chemistry, 2007, vol. 282, No. 5, pp. 2996-3003.
Brown, G. D., et al., "Isolation of a Desaturase Gene(s) from *Perkinsus marinus*", Journal of Shellfish Research, 2005, vol. 24, No. 2, p. 641.
Qi, B., et al., "Identification of a cDNA Encoding a Novel C18-$\Delta^9$ polyunsaturated Fatty Acid-Specific Elongating Activity from the Docosahexaenoic Acid (DHA)-Producing Microalga, *Isochrysis galbana*", FEBS Letters, 2002, vol. 510, pp. 159-165.
"Phaeodactylum tricornutum Condensing Enzyme (kas) mRNA, Complete cds", EMBL Database Accession No. AY746358, Jan. 1, 2006.
"*P. marinus* Genome [Online] Clone 19786", TIGR Database, *publication date unknown but at least in existence as of Nov. 2, 2005*.
"*P. marinus* Genome [Online] Clone 22469", TIGR Database, *publication date unknown but at least in existence as of Nov. 2, 2005*.

* cited by examiner

*Primary Examiner* — Elizabeth McElwain
(74) *Attorney, Agent, or Firm* — Connolly Bove Lodge & Hutz, LLP

(57) ABSTRACT

The invention relates to nucleic acid derived from *Perkinsus marinus* which encodes a 9-elongase, a Δ8-desaturase and a Δ5-desaturase enzyme. All of the coding sequences can be transcribed as a single transcript.

16 Claims, 2 Drawing Sheets

Various synthetic pathways for the biosynthesis of DHA (docosahexaenoic acid).

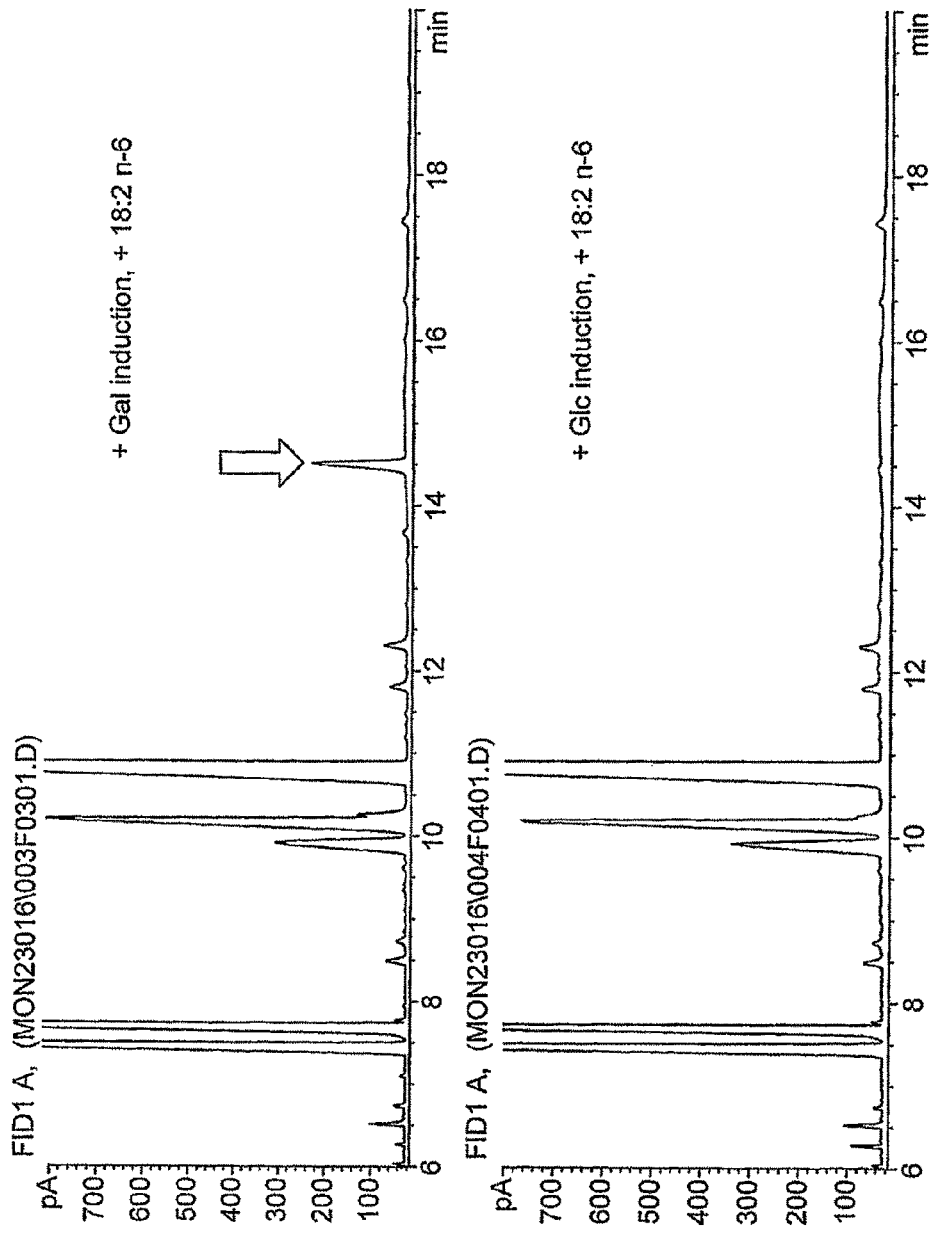

us 8,119,861 B2

ELONGASE AND USES THEREOF

RELATED APPLICATIONS

This application is a national stage application (under 35 U.S.C. §371) of PCT/GB2007/000491, filed Feb. 13, 2007, which claims benefit of United Kingdom application 0603160.3, filed Feb. 16, 2006.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence_Listing_16137_00001. The size of the text file is 62 KB, and the text file was created on Aug. 14, 2008.

FIELD OF THE INVENTION

The present invention relates to nucleic acid derived from *Perkinsus marinus* which encodes a 9-elongase, Δ8-desaturase and a Δ5-desaturase enzyme. All of the coding sequences can be transcribed as a single transcript, which simplifies the process of transforming cells required to express all three proteins. The invention also relates to the individual coding sequences and to proteins encoded by these sequences as well as to a process for converting linoleic acid to arachidonic acid.

DESCRIPTION OF RELATED ART

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter.

Polyunsaturated ω3-fatty acids and ω6-fatty acids are therefore an important constituent in animal and human nutrition.

Hereinbelow, polyunsaturated fatty acids are referred to as PUFA, PUFAs, LCPUFA or LCPUFAs (poly unsaturated fatty acids, PUFA, long chain poly unsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as docosahexaenoic acid (=DHA, $C22:6^{\Delta 4,7,10,13,16,19}$), eicosapentaenoic acid (=EPA, $C20:5^{\Delta 5,8,11,14,17}$), arachidonic acid (=ARA, $C20:4^{\Delta 5,8,11,14}$), dihomo-γ-linolenic acid ($C20:3^{\Delta 8,11,14}$) or docosapentaenoic acid (DPA, $C22:5^{\Delta 7,10,13,16,19}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, stroke or hypertension can be reduced markedly by adding these ω3-fatty acids to the food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Owing to the positive characteristics of the polyunsaturated fatty acids, there has been no lack of attempts in the past to make available genes which are involved in the synthesis of these fatty acids or triglycerides for the production of oils in various organisms with a modified content of unsaturated fatty acids. Thus, WO 91/13972 and its US equivalent describes a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, U.S. Pat. No. 5,614,393, WO 96/21022, WO 00/21557 and WO 99/27111 and the application for the production of fatty acids in transgenic organisms is described in WO 98/46763, WO 98/46764 and WO 98/46765. In this context, the expression of various desaturases and the formation of polyunsaturated fatty acids is also described and claimed in WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microalgae such as *Phaeodactylum tricornutum*, *Porphiridium* species, *Thraustochytrium* species, *Schizochytrium* species or *Crypthecodinium* species, ciliates such as *Stylonychia* or *Colpidium*, fungae such as *Mortierella*, *Entomophthora* or *Mucor* and/or mosses such as *Phy-*

*scomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible.

However, only limited amounts of the desired polyunsaturated fatty acids such as DPA, EPA or ARA can be produced with the aid of the abovementioned microorganisms, and, depending on the microorganism used, these are generally obtained as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA) (FIG. 1). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally β-oxidation to give the $C_{22}$ chain length. Thus what is known as Sprecher pathway (see FIG. 1) is, however, not suitable for the production in plants and microorganisms since the regulatory mechanisms are not known.

Depending on their desaturation pattern, the polyunsaturated fatty acids can be divided into two large classes, viz. ω6- or ω3-fatty acids, which differ with regard to their metabolic and functional activities (FIG. 1).

The starting material for the ω6-metabolic pathway is the fatty acid linoleic acid ($18:2^{\Delta 9,12}$) while the ω3-pathway proceeds via linolenic acid ($18:3^{\Delta 9,12,15}$). Linolenic acid is formed by the activity of an ω3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω3-desaturase) and must take up these fatty acids (essential fatty acids) via the food. Starting with these precursors, the physiologically important polyunsaturated fatty acids arachidonic acid (=ARA, $20:4^{\Delta 5,8,11,14}$), an ω6-fatty acid and the two ω3-fatty acids eicosapentaenoic acid (=EPA, $20:5^{\Delta 5,8,11,14,17}$) and docosahexaenoic acid (DHA, $22:6^{\Delta 4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), Entzündungen (Calder 2002, Proc. Nutr. Soc. 61, 345-358) and Arthritis (Cleland and James 2000, J. Rheumatol. 27, 2305-2307).

The elongation of fatty acids, by elongases, by 2 or 4 C atoms is of crucial importance for the production of $C_{20}$- and $C_{22}$-PUFAs, respectively. This process proceeds via 4 steps. The first step is the condensation of malonyl-CoA with the fatty-acid-acyl-CoA by ketoacyl-CoA synthase (KCS, hereinbelow referred to as elongase). This is followed by a reduction step (ketoacyl-CoA reductase, KCR), a dehydratation step (dehydratase) and a final reduction step (enoyl-CoA reductase). It has been postulated that the elongase activity affects the specificity and rate of the entire process (Millar and Kunst, 1997 Plant Journal 12:121-131).

There have been a large number of attempts in the past to obtain elongase genes. Millar and Kunst, 1997 (Plant Journal 12:121-131) and Millar et al. 1999, (Plant Cell 11:825-838) describe the characterization of plant elongases for the synthesis of monounsaturated long-chain fatty acids (C22:1) and for the synthesis of very long-chain fatty acids for the formation of waxes in plants ($C_{28}$-$C_{32}$). Descriptions regarding the synthesis of arachidonic acid and EPA are found, for example, in WO0159128, WO0012720, WO02077213 and WO0208401. The synthesis of polyunsaturated $C_{24}$-fatty acids is described, for example, in Tvrdik et al. 2000, JCB 149:707-717 or WO0244320.

Higher plants comprise polyunsaturated fatty acids such as linoleic acid ($18:2^{\Delta 9,12}$) and linolenic acid ($18:3^{\Delta 9,12,15}$). ARA, EPA and DHA are found not at all in the seed oil of higher plants, or only in miniscule amounts (E. Ucciani: Nouveau Dictionnaire des Huiles Végétales [New Dictionary of Vegetable Oils]. Technique & Documentation—Lavoisier, 1995. ISBN: 2-7430-0009-0). However, the production of LCPUFAs in higher plants, preferably in oil crops such as oilseed rape, linseed, sunflower and soybeans, would be advantageous since large amounts of high-quality LCPUFAs for the food industry, animal nutrition and pharmaceutical purposes might be obtained economically. To this end, it is advantageous to introduce, into oil crops, genes which encode enzymes of the LCPUFA biosynthesis via recombinant methods and to express them therein. These genes may encode for example Δ9-elongases, Δ8-desaturases and/or Δ5-desaturases. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans*.

The first transgenic plants which comprise and express genes encoding LCPUFA biosynthesis enzymes and which, as a consequence, produce LCPUFAs were described for the first time, for example, in DE-A-102 19 203 (process for the production of polyunsaturated fatty acids in plants). However, these plants produce LCPUFAs in amounts which require further optimization for processing the oils which are present in the plants.

As can be seen from FIG. 1, products of the ω6-pathway can be modified using appropriate desaturases and, if necessary, elongases to give ω3 fatty acids. Therefore, it would be exceedingly valuable to develop a product which makes possible the production of ARA in a genetically modified organism.

BRIEF DESCRIPTION OF THE DRAWINGS

FIG. 2 is a gas chromatography trace showing the conversion of Δ9,12-18:2 (linoleic acid) to Δ11,14-20:2 by heterologous expression of the *P. marinus* Δ9-elongase sequence (SEQ ID NO: 1, residues 7668 to 9200) in yeast induced either by galactose (top; "+Gal induction") or glucose (bottom; "+Glc induction").

DETAILED DESCRIPTION OF THE INVENTION

Figure 1:
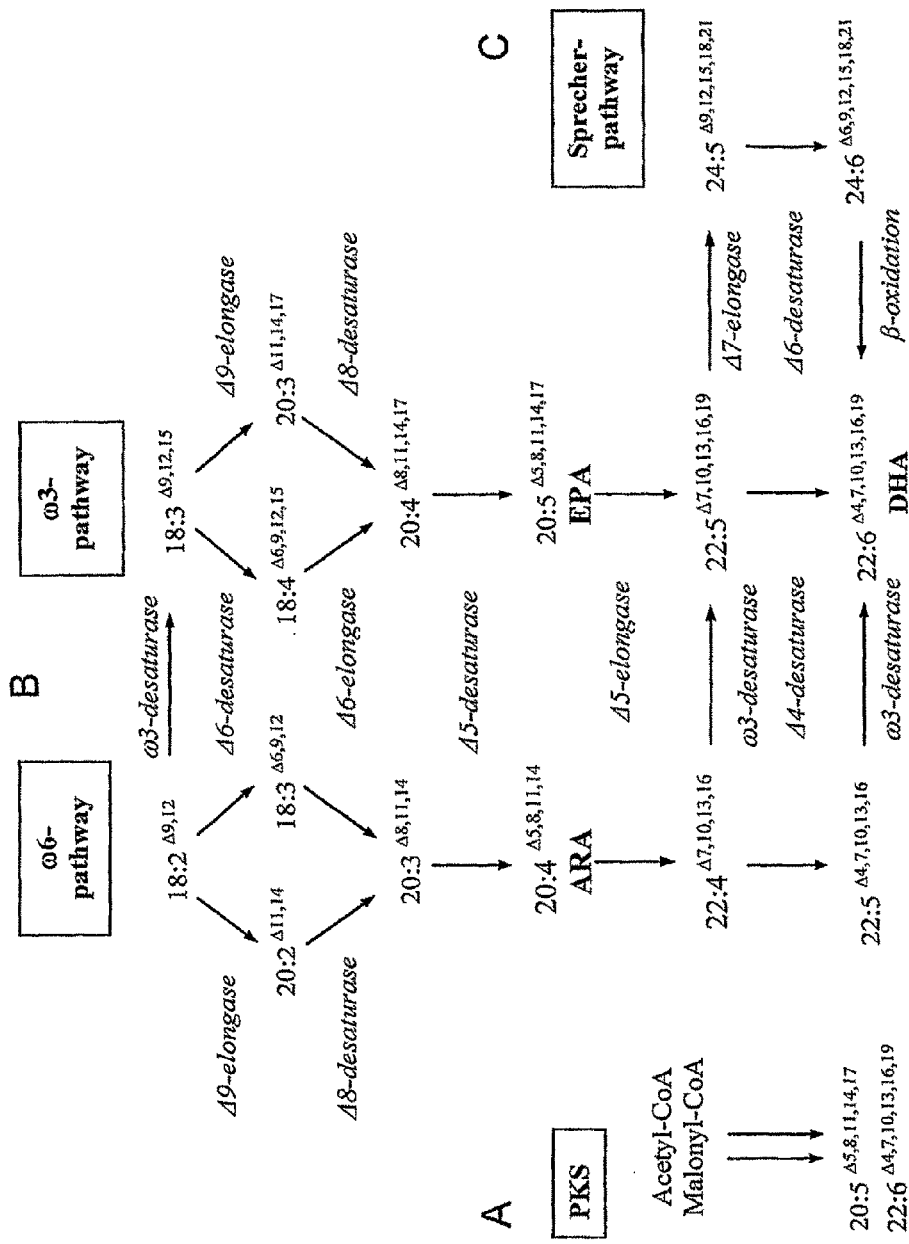
FIG. 1 shows various synthetic pathways for the biosynthesis of ω-6 and ω-3 fatty acids.

The oyster protozoan parasite *Perkinsus marinusi* is capable of synthesizing saturated and unsaturated fatty acids, including the essential fatty acid, arachidonic acid [20:4(n-6), via the Δ-8 desaturase pathway. Surprisingly the present inventors have found that *P. marinusi* contains nucleic encoding a Δ9-elongase, a Δ8-desaturase and a Δ5-desaturase which can all be transcribed as a single transcript. The full length sequence is shown as SEQ ID NO: 1.

Therefore, in a first aspect of the invention, there is provided an isolated nucleic acid sequence which encodes polypeptides with Δ9-elongase, Δ8-desaturase and Δ5-desaturase activity and which is selected from the group consisting of:

a) Anuclei acid sequence comprising nucleic acid residues 7668 to 12077 of SEQ ID NO: 1 or a homolog thereof;
b) a nucleic acid sequence which hybridizes under stringent conditions with a nucleic acid sequence comprising nucleic acid residues 7668 to 12077 of SEQ ID NO: 1;
c) an isolated nucleic acid sequence which encodes polypeptides with Δ9-elongase, Δ8-desaturase and Δ5-desaturase activity, wherein the polypeptides are selected from the group consisting of SEQ ID NOS 2, 3 and 4;
d) A derivative of a nucleic acid sequence of SEQ ID NO: 1 which encodes polypeptides with at least 40% identity at the amino acid level with SEQ ID NO: 2, SEQ ID NO: 3 and SEQ ID NO: 4; wherein said polypeptides have Δ9-elongase, Δ8-desaturase and Δ5-desaturase activity.

The advantage of the nucleic acid sequence of the present invention is that, although it encodes three separate enzymes, it can be transcribed as a single sequence, which makes it much simpler to prepare cloning and expression vectors expressing all three enzymes.

Preferably, the isolated nucleic acid sequence according to the invention is not identical to SEQ ID No. 1 (sequence 1047306867) itself.

In the context of the present invention "hybridizes under stringent conditions" is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least 75% or more homology to one another usually remain hybridized to one another. These stringent conditions are known to the skilled worker and described, for example, in Current Protocols in Molecular Biology, John Wiley & Sons, N.Y. (1989), 6.3.1-6.3.6. A preferred nonlimiting example of stringent hybridization conditions is hybridizations in 6×sodium chloride/sodium citrate (=SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the hybridization temperature is, depending on the type of nucleic acid, between 42° C. and 58° C. in aqueous buffer with a concentration of 0.1 to 5×SSC (pH 7.2). If organic solvents, for example 50% formamide, are present in the abovementioned buffer, the temperature under standard conditions is approximately 42° C. The hybridization conditions for DNA:DNA hybrids, for example, are 0.1×SSC and 20° C. to 45° C., preferably 30° C. to 45° C. The hybridization conditions for DNA: RNA hybrids are, for example, 0.1×SSC and 30° C. to 55° C., preferably 45° C. to 55° C. The abovementioned hybridization conditions are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

Furthermore, when the present specification refers to isolated nucleic acid molecules of a nucleotide sequence which hybridize with one of the nucleotide sequences shown in SEQ ID NO: 1, SEQ ID NO: 3 or with a part thereof under stringent conditions, "a part thereof" is understood as meaning, in accordance with the invention, that at least 25 base pairs (=bp), 50 bp, 75 bp, 100 bp, 125 bp or 150 bp, preferably at least 175 bp, 200 bp, 225 bp, 250 bp, 275 bp or 300 bp, especially preferably 350 bp, 400 bp, 450 bp, 500 bp or more base pairs are used for the hybridization.

In the context of the present invention "Homologs" of the nucleic acid sequence with the sequence SEQ ID NO: 1 means, for example, allelic variants with at least approximately 50 or 60%, preferably at least approximately 60 or 70%, more preferably at least approximately 70 or 80%, 90% or 95% and even more preferably at least approximately 85%, 86%, 87%, 88%, 89%, 90%, 91%, 92%, 93%, 94%, 95%, 96%, 97%, 98%, 99% or more identity or homology with a nucleotide sequence shown in SEQ ID NO: 1.

"Allelic variants" comprise in particular functional variants which can be obtained by deletion, insertion or substitution of nucleotides from/into the sequence, it being intended, however, that the enzyme activity of the resulting proteins which are synthesized is advantageously retained for the insertion of one or more genes.

"Homologs" also means bacterial, fungal and plant homologs, truncated sequences, single-stranded DNA or RNA of the coding and noncoding DNA sequence and derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

In order to determine the percentage of homology (=identity) of two amino acid sequences, the sequences are written one under the other for an optimal comparison (for example, gaps may be introduced into the sequence of a protein or of a nucleic acid in order to generate an optimal alignment with the other protein or the other nucleic acid). Then, the amino acid residue or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of positions which the sequences share (i.e. % homology=number of identical positions/total number of positions×100). The terms homology and identity are therefore to be considered as synonymous.

The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence 0gy values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

In the context of the present invention "Δ9-elongase, Δ8-desaturase and Δ5-desaturase activity" is understood as meaning that a protein encoded by a derivative of SEQ ID NO:1 or nucleic acid residues 7668 to 12077 of SEQ ID NO: 1 retains an enzymatic activity of at least 10%, preferably 20%, especially preferably 30% and very especially 40% in comparison with the proteins/enzymes encoded by the sequence SEQ ID NO: 1 or nucleic acid residues 7668 to 12077 of SEQ ID NO: 1 and can thus catalyse the conversion of linoleic acid to arachidonic acid.

Although it is often extremely useful to transcribe nucleic acid encoding polypeptides with Δ9-elongase, Δ8-desaturase and Δ5-desaturase activity as a single sequence, there may be some circumstances in which it is preferable to make use of nucleic acid encoding a single enzyme, i.e. a Δ9-elongase, a Δ8-desaturase or a Δ5-desaturase.

Therefore, in a second aspect of the invention there is provided an isolated nucleic acid sequence which encodes a polypeptide with Δ9-elongase activity and which is selected from the group consisting of:
a) a sequence comprising nucleic acid residues 7668 to 9200 of SEQ ID NO: 1, SEQ ID NO: 9 or a homolog of one of these;
b) nucleic acid sequences which hybridize under stringent conditions with a nucleic acid sequence comprising residues 7668 to 9200 of SEQ ID NO: 1 or SEQ ID NO: 9;
c) an isolated nucleic acid sequence which encodes polypeptides with Δ9-elongase, activity, wherein the polypeptide comprises SEQ ID NO: 2 or SEQ ID NO: 10;
d) A derivative of a a sequence comprising nucleic acid residues 7668 to 9200 of SEQ ID NO: 1 or SEQ ID NO: 9, which encodes a polypeptide with at least 40% identity at the amino acid level with SEQ ID NO: 2 or SEQ ID NO: 10; wherein said polypeptide has Δ9-elongase activity.

In a third aspect of the invention, there is provided an isolated nucleic acid sequence which encodes a polypeptide with Δ8-desaturase activity and which is selected from the group consisting of:
a) a sequence comprising nucleic acid residues 9351 to 10724 of SEQ ID NO: 1 or a homolog thereof;
b) nucleic acid sequences which hybridize under stringent conditions with a nucleic acid sequence comprising residues 9351 to 10724 of SEQ ID NO: 1;
c) an isolated nucleic acid sequence which encodes polypeptides with Δ8-desaturase activity, wherein the polypeptide comprises SEQ ID NO: 3;
d) A derivative of a a sequence comprising nucleic acid residues 9351 to 10724 of SEQ ID NO: 1 which encodes a polypeptide with at least 40% identity at the amino acid level with SEQ ID NO: 3; wherein said polypeptide has Δ8-desaturase activity.

In a fourth aspect of the invention, there is provided an isolated nucleic acid sequence which encodes a polypeptide with Δ5-desaturase activity and which is selected from the group consisting of:
a) a sequence comprising nucleic acid residues 10842 to 12077 of SEQ ID NO: 1 or a homolog thereof;
b) nucleic acid sequences which hybridize under stringent conditions with a nucleic acid sequence comprising residues 10842 to 12077 of SEQ ID NO: 1;
c) an isolated nucleic acid sequence which encodes polypeptides with Δ5-desaturase activity, wherein the polypeptide comprises SEQ ID NO: 4;
d) A derivative of a a sequence comprising nucleic acid residues 10842 to 12077 of SEQ ID NO: 1 which encodes a polypeptide with at least 40% identity at the amino acid level with SEQ ID NO: 4; wherein said polypeptide has Δ5-desaturase activity.

In still another aspect of the invention there is provided a polypeptide which is encoded by a nucleic acid sequence of any of the first to fourth aspects of the invention.

Advantageously, the polypeptide encoded by these nucleic acid molecules have at least approximately 50%, preferably at least approximately 60% and more preferably at least approximately 70%, 80% or 90% and most preferably at least approximately 85%, 86%, 87%, 88%, 89%, 90%, 91%, 92%, 93%, 94%, 95%, 96%, 97%, 98%, 99% or more identity with the amino acid sequences shown in SEQ ID NO: 2, SEQ ID NO: 3, SEQ ID NO: 4 or SEQ ID NO: 9.

The nucleic acid sequences used in the process are advantageously introduced into an expression cassette which makes possible the expression of the nucleic acids in organisms such as microorganisms or plants.

Therefore, in another aspect of the invention there is provided a gene construct comprising a nucleic acid sequence which encodes one or more polypeptides with Δ9-elongase, Δ8-desaturase and/or Δ5-desaturase activity as set out above, operably linked with one or more regulatory sequences.

In the expression cassette, the nucleic acid sequence which encodes Δ9-elongase, Δ8-desaturase and/or Δ5-desaturase, is linked operably with one or more regulatory sequences, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it is expressed and/or overexpressed immediately. For example, these regulatory sequences take the form of sequences to which inductors or repressors bind, thus controlling the expression of the nucleic acid. In addition to these novel regulatory sequences, or instead of these sequences, the natural regulatory elements of these sequences may still be present before the actual structural genes and, if appropriate, may have been genetically modified in such a way that their natural regulation is eliminated and the expression of the genes is enhanced. However, the expression cassette (=expression construct=gene construct) can also be simpler in construction, that is to say no additional regulatory signals have been inserted before the nucleic acid sequence or its derivatives, and the natural promoter together with its regulation was not removed. Instead, the natural regulatory sequence has been mutated in such a way that regulation no longer takes place and/or gene expression is enhanced. These modified promoters can also be positioned on their own before the natural gene in the form of part-sequences (=promotor with parts of the nucleic acid sequences used in accordance with the invention) in order to enhance the activity. Moreover, the gene construct may advantageously also comprise one or more what are known as enhancer sequences in operable linkage with the promoter, which make possible an enhanced expression of the nucleic acid sequence.

Additional advantageous sequences, such as further regulatory elements or terminator sequences, may also be inserted at the 3' end of the DNA sequences. One or more sequences encoding enzymes which catalyse the conversion of ARA to an ω3-unsaturated fatty acid such as EPA or DHA may also be present. Thus, for example, sequences encoding a Δ5-elongase, ω3-desaturase and/or Δ4-desaturase, may be present in one or more copies of the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

The regulatory sequences include, in particular, plant sequences such as promoter and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

Useful regulatory sequences are present, for example, in promoters such as the cos, tac, trp, tet, trp-tet, lpp, lac, lpp-lac, lacIq, T7, T5, T3, gal, trc, ara, SP6, λ-PR or λ-PL promoter and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscissic acid-inducible) or WO 93/21334 (ethanol- or cyclohexenol-inducible) promoters. Further suitable plant promoters are the cytosolic FBPase promoter or the ST-LSI promoter of potato (Stockhaus et al., EMBO J. 8, 1989, 2445), the *glycine max* phosphoribosylpyrophosphate amidotransferase promoter (Genbank Accession No. U87999) or the node-specific promoter described in EP-A-0 249 676.

Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arabidopsis* oleosin promoter), U.S. Pat. No. 5,504,200 (*Phaseolus vulgaris* phaseolin promoter), WO 91/13980 (Brassica Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890.

In principle, it is possible to use all natural promoters together with their regulatory sequences, such as those mentioned above. It is also possible and advantageous to use synthetic promoters, either in addition or alone, in particular when they mediate seed-specific expression, such as those described in WO 99/16890.

In order to achieve a particularly high ARA content, especially in transgenic plants, the genes should advantageously be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Preferred promoters are listed hereinbelow: USP (=unknown seed protein) and vicilin (*Vicia faba*) [Bäumlein et al., Mol. Gen Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Bäumlein et al., Plant J., 2, 2, 1992], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, it is usually necessary for each of the nucleic acids which encodes a protein of interest to be expressed under the control of a separate promoter, preferably a promoter which differs from the other promoters, since repeating sequence motifs can lead to instability of the T-DNA, or to recombination events. This is one reason why the nucleic acid of the present invention is particularly advantageous since sequences encoding Δ9-elongase, Δ8-desaturase and Δ5-desaturase can be transcribed as a single unit needing only one promoter. It will, of course, be necessary for other genes encoding, for example, Δ5-elongase, ω3-desaturase and/or Δ4-desaturase to be under the control of separate promoters.

In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator sequence. Such advantageous constructs are disclosed, for example, in DE 101 02 337 or DE 101 02 338. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette. This, however, may lead to undesired recombination events.

As described above, the transcription of the genes which have been introduced should advantageously be terminated by suitable terminator sequences at the 3' end of the biosynthesis genes which have been introduced (behind the stop codon). An example of a sequence which can be used in this context is the OCS 1 terminator sequence. As is the case with the promoters, different terminator sequences should be used for each gene.

The gene construct of the present invention may also comprise biosynthesis genes of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) and desaturase(s) such as $\Delta 4$-desaturase, $\Delta 5$-desaturase, $\Delta 6$-desaturase, $\Delta 8$-desaturase, $\Delta 9$-desaturase, $\Delta 12$-desaturase or $\Delta 6$-elongase.

These additional nucleic acids or genes can be cloned into the expression cassettes, which are then used for transforming plants with the aid of vectors such as *Agrobacterium*.

Here, the regulatory sequences or factors can, as described above, preferably have a positive effect on, and thus enhance, the expression genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plants or else be introduced into a vector.

Therefore, in yet another aspect of the invention, there is provided a vector comprising a nucleic acid or a gene construct in any of the aspects of the invention described above.

In one embodiment, the vector may be a cloning vector.

The nucleic acid sequence(s) of the invention may be introduced alone, or preferably, in combination with an expression cassette (nucleic acid construct) into an organism. To introduce the nucleic acids, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step.

Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreen. In accordance with the invention, Bin19, pBI101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments which have been prepared in a similar manner, using ligase. In this context, a particular nucleic acid construct, or vector or plasmid construct, can have one or else more than one codogenic gene segment. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

The nucleic acids of the invention can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient producers of ARA.

A series of mechanisms exist by which modification of the Δ9-elongase, Δ8-desaturase and Δ5-desaturase proteins is possible, so that the yield, production and/or production efficiency of ARA in a plant, preferably in an oil crop plant or a microorganism, can be influenced directly owing to these modified proteins. The number or activity of the proteins or genes can be increased, so that greater amounts of the gene products and, ultimately, greater amounts of the compounds of the general formula I are produced. A de novo synthesis in an organism which has lacked the activity and ability to biosynthesize the compounds prior to introduction of the corresponding gene(s) is also possible. This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which make possible a different gene expression in the course of time, for example as a function of the degree of maturity of a seed or an oil-storing tissue.

Owing to the introduction of a gene encoding Δ9-elongase, Δ8-desaturase and/or Δ5-desaturase into an organism, alone or in combination with other genes in a cell, it is not only possible to increase biosynthesis flux towards the end product, but also to increase, or to create de novo the corresponding triacylglycerol composition. Likewise, the number or activity of other genes which are involved in the import of nutrients which are required for the biosynthesis of one or more fatty acids, oils, polar and/or neutral lipids, can be increased, so that the concentration of these precursors, cofactors or intermediates within the cells or within the storage compartment is increased, whereby the ability of the cells to produce ARA as described below is enhanced further. By optimizing the activity or increasing the number of one or more genes encoding Δ9-elongase, Δ8-desaturase and/or Δ5-desaturase which are involved in the biosynthesis ARA, or by destroying the activity of one or more genes which are involved in the degradation of ARA, an enhanced yield, production and/or efficiency of production of fatty acid and lipid molecules in organisms, advantageously in plants, is made possible.

Nucleic acids which can advantageously be used in the process are derived from bacteria, fungi, diatoms, animals such as *Caenorhabditis* or *Oncorhynchus* or plants such as algae or mosses, such as the genera *Shewanella, Physcomitrella, Thraustochytrium, Fusarium, Phytophthora, Ceratodon, Mantoniella, Ostreococcus, Isochrysis, Aleurita, Muscarioides, Mortierella, Borago, Phaeodactylum, Crypthecodinium*, specifically from the genera and species *Oncorhynchus mykiss, Xenopus laevis, Ciona intestinalis, Thalassiosira pseudonona, Mantoniella squamata, Ostreococcus* sp., *Ostreococcus tauri, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Borago officinalis, Phaeodactylum tricornutum, Caenorhabditis elegans* or especially advantageously from *Oncorhynchus mykiss, Euglena gracilis, Thalassiosira pseudonona* or *Crypthecodinium cohnii*.

In an alternative embodiment, the vector may be an expression vector designed to transform an organism in which the nucleic acid is to be expressed and linoleic acid converted to ARA.

These advantageous vectors, preferably expression vectors, comprise the nucleic acid(s) which encode the Δ9-elongase, Δ8-desaturase and/or Δ5-desaturase and which are described in the first to fourth aspects of the invention.

As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids.

In the present description, where the term "plasmid" is used, it should be understood that plasmids can be substituted for other types of expression vector, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process comprise the nucleic acids described below or the above-described gene construct in a form which is suitable for expressing the nucleic acids used in a host cell, which means that the recombinant expression vectors comprise one or more regulatory sequences, selected on the basis of the host cells used for the expression, which regulatory sequence(s) is/are linked operably with the nucleic acid sequence to be expressed. In a recombinant expression vector, "linked operably" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the desired expression level of the protein and the like.

The recombinant expression vectors used can be designed for the expression of Δ9-elongase, Δ8-desaturase and/or Δ5-desaturase in prokaryotic or eukaryotic cells. This is advantageous since intermediate steps of the vector construction are frequently carried out in microorganisms for the sake of simplicity. For example, the Δ9-elongase, Δ8-desaturase and/or Δ5-desaturase gene can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.:583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or non-fusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) und pRIT5 (Pharmacia, Piscataway, N.J.), where glutathione S-transferase (GST), maltose-E binding protein and protein A, respectively, is fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples for vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, Δ9-elongase, Δ8-desaturase and/or Δ5-desaturase can be expressed in insect cells using Baculovirus vectors. Baculovirus expression vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

The abovementioned vectors are only a small overview over suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2. edition, Cold Spring Harbor Laboratory, Cold Spring Harbor Laboratory Press, Cold Spring Harbor, N.Y., 1989.

In a further embodiment of the process, the Δ9-elongase, Δ8-desaturase and/or Δ5-desaturase can be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminator sequences which are functionally active in plants are also suitable.

Since plant gene expression is very often not limited to the transcriptional level, a plant expression cassette preferably comprises other sequences which are linked operably, such as translation enhancers, for example the overdrive sequence, which enhances the tobacco mosaic virus 5'-untranslated leader sequence, which increases the protein/RNA ratio (Gallie et al., 1987, Nucl. Acids Research 15:8693-8711).

As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the Rubisco subunit, which is described in U.S. Pat. No. 4,962,028.

Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmid reticulum, elaioplasts, peroxisomes and other compartments of plant cells.

As described above, plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890.

As described above, it may be advantageous to include in an expression cassette nucleic acid encoding enzymes capable of coverting ARA to ω3-unsaturated fatty acids such as EPA or DHA. Thus, for example the expression cassette may also include nucleic acid encoding a Δ5-elongase, ω3-desaturase and/or Δ4-desaturase. Such expression cassettes can be introduced via the simultaneous transformation of a plurality of individual expression constructs or, preferably, by combining a plurality of expression cassettes on one construct. Also, a plurality of vectors can be transformed with in each case a plurality of expression cassettes and then transferred into the host cell.

Other promoters which are likewise especially suitable are those which bring about a plastid-specific expression, since plastids constitute the compartment in which the precursors and some end products of lipid biosynthesis are synthesized. Suitable promoters, such as the viral RNA polymerase promoter, are described in WO 95/16783 and WO 97/06250, and the cIpP promoter from *Arabidopsis*, described in WO 99/46394.

Vector DNA can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

In a further aspect of the invention there is provided a transgenic non human organism comprising at least one nucleic acid, gene construct or vector according to a previous aspect of the invention.

The transgenic nonhuman organism may be a microorganism, a nonhuman animal or a plant.

Host cells which are suitable in principle for taking up the nucleic acid according to the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are preferably used, especially plants, for example plants such as oil crops, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassaya, pepper, Tagetes, Solanacea plants such as potato, tobacco, eggplant and tomato, *Vicia* species, pea, alfalfa, bushy plants (coffee, cacao, tea), *Salix* species, trees (oil palm, coconut), and perennial grasses and fodder crops. Especially preferred plants according to the invention are oil crops such as soybean, peanut, oilseed rape, canola, linseed, hemp, evening primrose, sunflower, safflower, trees (oil palm, coconut).

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separate from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid). In various embodiments, the isolated Δ9-elongase, Δ8-desaturase or Δ5-desaturase molecule can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The same applies to other nucleic acid sequences which may be included in an expression cassette, for example sequences encoding a Δ5-elongase, ω3-desaturase and/or Δ4-desaturase The nucleic acid molecules of the present invention, for example a nucleic acid molecule with a nucleotide sequence of SEQ ID NO: 1 or residues 7668 to 12077 thereof, or the parts of SEQ ID NO: 1 specified in the second to fourth aspects of the invention, can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe and standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process.

Moreover, a nucleic acid molecule from *Perkinsus marinus* comprising a complete sequence of SEQ ID NO: 1 or a part thereof can be isolated by polymerase chain reaction, where oligonucleotide primers which are used on the basis of this sequence or parts thereof (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.).

Synthetic oligonucleotide primers for the amplification by means of polymerase chain reaction can be generated based on one of the sequences shown in SEQ ID NO: 1 or with the aid of the amino acid sequences detailed in SEQ ID NO: 2, SEQ ID NO: 3 and SEQ ID NO: 4. Particularly suitable primers are shown in the Examples as SEQ ID NO: 5 and SEQ ID NO: 6.

A nucleic acid according to the invention can be amplified by standard PCR amplification techniques using cDNA or, alternatively, genomic DNA as template (SEQ ID NO 9) and suitable oligonucleotide primers (SEQ ID NO: 5 and SEQ ID NO: 6). The nucleic acid amplified thus can be cloned into a suitable vector and characterized by means of DNA sequence analysis. Oligonucleotides which correspond to a desaturase or elongase nucleotide sequence can be generated by standard synthetic methods, for example using an automatic DNA synthesizer.

The abovementioned nucleic acids and protein molecules with Δ9-elongase, Δ8-desaturase and/or Δ5-desaturase activity may be used in a process for the production of ARA from linoleic acid in transgenic organisms.

Therefore, in a further aspect of the invention, there is provided a process for the conversion of linoleic acid or a derivative thereof to arachidonic acid or a derivative thereof in an organism, the process comprising introducing into an organism which comprises linoleic acid at least one nucleic acid sequence comprising:

a) SEQ ID NO: 1 (Full sequence 1047306867), sequence comprising nucleic acid residues 7668 to 12077 of SEQ ID NO: 1 or a homolog of one of these;

b) nucleic acid sequences which hybridize under stringent conditions with a nucleic acid sequence of SEQ ID NO: 1 or a sequence comprising nucleic acid residues 7668 to 12077 of SEQ ID NO: 1;

c) an isolated nucleic acid sequence which encodes polypeptides with Δ9-elongase, Δ8-desaturase and Δ5-desaturase activity, wherein the polypeptides are selected from the group consisting of SEQ ID NOS 2, 3 and 4;

d) A derivative of a nucleic acid sequence of SEQ ID NO: 1 which encodes polypeptides with at least 40% identity at the amino acid level with SEQ ID NO: 2, SEQ ID NO: 3 and SEQ ID NO: 4; wherein said polypeptides have Δ9-elongase, Δ8-desaturase and Δ5-desaturase activity.

and expressing said nucleic acid sequence.

In the context of the present invention, a "derivative" of linoleic or arachidonic acid is a compound in which the OH of the carboxylic acid moiety is replaced by a moiety $R^1$, wherein:

$R^1$ is coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

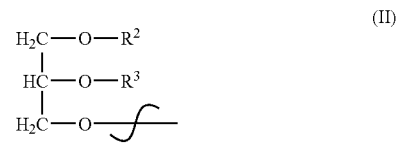

in which $R^2$=hydrogen, lysophosphatidyl choline, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of one another are a radical of the formula Ia:

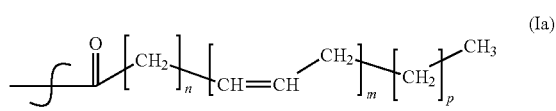

in which n=2, 3, 4, 5, 6, 7 or 9, m=2, 3, 4, 5 or 6 and p=0 or 3;

and wherein an oxygen in the $R^1$ radical may be replaced by sulphur such that $R^1$ is bonded to the remainder of the molecule via a thioester linkage.

The processes according to the invention preferably yields total ARA in a content of at least 1% by weight, advantageously at least 3% by weight, based on the total fatty acids in the transgenic organisms, preferably in a transgenic plant.

Since a plurality of reaction steps are performed by the starting compounds linoleic acid ($18:2^{\Delta 9,12}$) in the process according to the invention, ARA ($20:4^{\Delta 5,8,11,14}$) is not obtained as a pure product; minor traces of the precursors are always present in the end product.

Chemically pure ARA can also be synthesized by the process described above. To this end, ARA or a derivative thereof is isolated from the organisms, such as the microorganisms or the plants or the culture medium in or on which the organisms have been grown, or from the organism and the culture medium, in the known manner, for example via extraction, distillation, crystallization, chromatography or a combination of these methods. These chemically ARA or ARA derivatives are advantageous for applications in the food industry sector, the cosmetic sector and especially the pharmacological industry sector.

The process may include additional steps of converting the ARA to an ω-3 fatty acid by introducing into the organism nucleic acid encoding a ω-3 desaturase and optionally a Δ5-elongase and/or a Δ4-elongase and/or a Δ4-desaturase.

In a further aspect the invention comprises a process for the conversion of $18:2^{\Delta 9,12}$ (linoleic acid) to $20:2^{\Delta 11,14}$, the process comprising introducing into an organism which comprises linoleic acid at least one nucleic acid sequence which encodes a polypeptide having Δ9-elongase activity and which comprises:
  a) a sequence comprising nucleic acid residues 7668 to 9200 of SEQ ID NO: 1, SEQ ID NO: 9 or a homolog of one of these;
  b) a nucleic acid sequence which hybridizes under stringent conditions with a nucleic acid sequence comprising residues 7668 to 9200 of SEQ ID NO: 1 or SEQ ID NO: 9;
  c) an isolated nucleic acid sequence which encodes a polypeptide with Δ9-elongase activity, wherein the polypeptide comprises SEQ ID NO: 2 or SEQ ID NO: 10;
  d) A derivative of a a sequence comprising nucleic acid residues 7668 to 9200 of SEQ ID NO: 1 or SEQ ID NO: 9 which encodes a polypeptide with at least 40% identity at the amino acid level with SEQ ID NO: 2 or SEQ ID NO: 10; wherein said polypeptide has Δ9-elongase activity;
and expressing said nucleic acid sequence.

In a further aspect of the invention there is provided a process for the conversion of $20:2^{\Delta 11,14}$ to $20:3^{\Delta 8,11,14}$, the process comprising introducing into an organism which comprises $20:2^{\Delta 11,14}$, or which comprises linoleic acid and a Δ9 elongase, an isolated nucleic acid sequence which encodes a polypeptide with Δ8-desaturase activity and which is selected from the group consisting of:
  a) a sequence comprising nucleic acid residues 9351 to 10724 of SEQ ID NO: 1 or a homolog thereof;
  b) nucleic acid sequences which hybridize under stringent conditions with a nucleic acid sequence comprising residues 9351 to 10724 of SEQ ID NO: 1;
  c) an isolated nucleic acid sequence which encodes polypeptides with Δ8-desaturase activity, wherein the polypeptide comprises SEQ ID NO: 3;
  d) A derivative of a a sequence comprising nucleic acid residues 9351 to 10724 of SEQ ID NO: 1 which encodes a polypeptide with at least 40% identity at the amino acid level with SEQ ID NO: 3; wherein said polypeptide has Δ8-desaturase activity; and
expressing said nucleic acid sequence.

In a further aspect of the invention, there is provided a process for the conversion of $20:3^{\Delta 8,11,14}$ to $20:4^{\Delta 5,8,11,14}$ (ARA), the process comprising introducing into an organism which comprises $20:3^{\Delta 8,11,14}$ or which comprises $20:2^{\Delta 11,14}$ and a Δ8-desaturase, or which comprises linoleic acid, a Δ9 elongase and a Δ8-desaturase, an isolated nucleic acid sequence which encodes a polypeptide with Δ5-desaturase activity and which is selected from the group consisting of:
  a) a sequence comprising nucleic acid residues 10842 to 12077 of SEQ ID NO: 1 or a homolog thereof;
  b) nucleic acid sequences which hybridize under stringent conditions with a nucleic acid sequence comprising residues 10842 to 12077 of SEQ ID NO: 1;
  c) an isolated nucleic acid sequence which encodes polypeptides with Δ5-desaturase activity, wherein the polypeptide comprises SEQ ID NO: 4;
  d) A derivative of a sequence comprising nucleic acid residues 10842 to 12077 of SEQ ID NO: 1 which encodes a polypeptide with at least 40% identity at the amino acid level with SEQ ID NO: 4; wherein said polypeptide has Δ5-desaturase activity.
and expressing said nucleic acid sequence.

The process may include additional steps of converting the ARA to an ω-3 fatty acid by introducing into the organism nucleic acid encoding a ω-3 desaturase and optionally a Δ5-elongase and/or a Δ4-elongase and/or a Δ4-desaturase.

For the processes set out above, it has been found that expression has been most effectively achieved using induction with galactose.

Suitable organisms for the production in the process according to the invention are, in principle, any organisms such as microorganisms, nonhuman animals or plants.

Plants which are suitable are, in principle, all those plants which are capable of synthesizing fatty acids, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Euglenaceae, Prasinophyceae or vegetable plants or ornamentals such as Tagetes.

Examples which may be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus columa* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricomutum*, Ditrichaceae, such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euglenaceae, such as the genera *Ascoglena, Astasia, Colacium, Cyclidiopsis, Euglena, Euglenopsis, Hyalaphacus, Khawkinea, Lepocinclis, Phacus, Strombomonas, Trachelomonas*, for example the genus and species *Euglena gracilis*; Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassaya] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, Mimosa lebbeck, Mimosa speciosa, Medicago sativa, Medicago falcata, Medicago varia* [alfalfa] *Glycine max Dolichos soja, Glycine gracilis, Glycine hispida, Phaseolus max, Soja hispida* or *Soja max* [soybean], Funariaceae, such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria piano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium colora dense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elaeis*, for example the genus and species *Elaeis guineensis* [oil palm], Papaveraceae, such as, for example, the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondi, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize] *Triticum aestivum, Triticum durum, Triticum turgidum, Triticum hybemum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia [macadamia]*, Prasinophyceae, such as the genera *Nephroselmis, Prasinococcus, Scherffelia, Tetraselmis, Mantoniella, Ostreococus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae, such as the genus *Coffea*, for example the genera and species *Coffea* spp., *Coffea arabica, Coffea canephora* or *Coffea liberica* [coffee], Scrophulariaceae, such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae, such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuate, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant] *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Advantageous microorganisms are, for example, fungi selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacharomycetaceae, Saprolegniaceae, Schizosacharomycetaceae, Sodariaceae or Tuberculariaceae.

Examples of microorganisms which may be mentioned are those from the groups Choanephoraceae, such as the genera *Blakeslea, Choanephora*, for example the genera and species *Blakeslea trispora, Choanephora cucurbitarum, Choanephora infundibulifera* var. *cucurbitarum*, Mortierellaceae, such as the genus *Mortierella*, for example the genera and species *Mortierella isabellina, Mortierella polycephala, Mortierella ramanniana, Mortierella vinacea, Mortierella zonata*, Pythiaceae, such as the genera *Phytium, Phytophthora*, for example the genera and species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae*, Saccharomycetaceae, such as the genera *Hansenula, Pichia, Saccharomyces, Saccharomycodes, Yarrowia*, for example the genera and species *Hansenula anomala, Hansenula californica, Hansenula canadensis, Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula satumus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia hoistii, Pichia jadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodan-* ensis, *Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica, Schizosacharomycetaceae* such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe*, Thraustochytriaceae such as the genera *Althornia, Aplanochytrium, Japonochytrium, Schizochytrium, Thraustochytrium* e.g. the species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense.*

Further advantageous microorganisms are, for example, bacteria selected from the group of the families Bacillaceae, Enterobacteriacae or Rhizobiaceae.

Examples which may be mentioned are the following microorganisms selected from the group consisting of: Bacillaceae, such as the genus *Bacillus*, for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia*, for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter sp., Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli-mutabile, Escherichia fergusonii, Escherichia hermannii, Escherichia* sp., *Escherichia vulneris, Klebsiella aerogenes, Klebsiella edwardsii* subsp. *atlantae, Klebsiella omithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella cholera esuis* subsp. *bongori, Salmonella cholera esuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae, such as the genera *Agrobacterium, Carbophilus, Chelatobacter, Ensifer, Rhizobium, Sinorhizobium*, for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense.*

Further examples of advantageous microorganisms for the process according to the invention are protists or diatoms selected from the group of the families Dinophyceae, Turaniellidae or Oxytrichidae, such as the genera and species: *Crypthecodinium cohnii, Phaeodactylum tricomutum, Stylo-*

*nychia mytilus, Stylonychia pustulata, Stylonychia putrina, Stylonychia notophora, Stylonychia* sp., *Colpidium campylum* or *Colpidium* sp.

Those which are advantageously applied in the process according to the invention are transgenic organisms such as fungi, such as *mortierella* or *thraustrochytrium*, yeasts such as *Saccharomyces* or *Schizosaccharomyces*, mosses such as *Physcomitrella* or *Ceratodon*, nonhuman animals such as *Caenorhabditis*, algae such as *Nephroselmis, Pseudoscourfielda, Prasinococcus, Scherffelia, Tetraselmis, Mantoniella, Ostreococcus, Crypthecodinium* or *Phaeodactylum* or plants such as dicotyledonous or monocotyledonous plants. Organisms which are especially advantageously used in the process according to the invention are organisms which belong to the oil-producing organisms, that is to say which are used for the production of oil, such as fungi, such as *Mortierelia* or *Thraustochytrium*, algae such as *Nephroselmis, Pseudoscourfielda, Prasinococcus, Scherffelia, Tetraselmis, Mantoniella, Ostreococcus, Crypthecodinium, Phaeodactylum,* or plants, in particular plants, preferably oilseed or oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica,* evening primrose, verbascum, thistle, wild roses, hazelnut, almond, macadamia, avocado, bay, pumpkin/squash, linseed, soybean, pistachios, borage, trees (oil palm, coconut or walnut) or arable crops such as maize, wheat, rye, oats, triticale, rice, barley, cotton, cassaya, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica,* evening primrose, pumpkin/squash, linseed, soybean, borage, trees (oil palm, coconut). Especially preferred for the process are plants which are high in C18:2-fatty acids, such as sunflower, safflower, tobacco, verbascum, sesame, cotton, pumpkin/squash, poppy, evening primrose, walnut, linseed, hemp or thistle. Very especially preferred plants are plants such as safflower, sunflower, poppy, evening primrose, walnut, linseed or hemp.

It is also be advantageous for the above-described method according to the invention additionally to introduce, into the organism, further nucleic acids which encode enzymes of the fatty acid or lipid metabolism, in addition to the nucleic acids of the first to fourth aspects of the invention.

Such nucleic acids are advantageously derived from plants such as algae, for example algae of the family of the Prasinophyceae such as the genera *Heteromastix, Mammella, Mantonielia, Micromonas, Nephroselmis, Ostreococcus, Prasinocladus, Prasinococcus, Pseudoscourfielda, Pycnococcus, Pyramimonas, Scherffelia* or *Tetraselmis* such as the genera and species *Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus* sp. *Prasinocladus ascus, Prasinocladus lubricus, Pycnococcus provasolii, Pyramimonas amylifera, Pyramimonas disomata, Pyramimonas obovata, Pyramimonas orientalis, Pyramimonas parkeae, Pyramimonas spinifera, Pyramimonas* sp., *Tetraselmis apiculata, Tetraselmis carteriaformis, Tetraselmis chui, Tetraselmis convolutae, Tetraselmis desikacharyl, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa fo. rubens* or *Tetraselmis* sp. or from algae of the family Euglenaceae such as the genera *Ascoglena, Astasia, Colacium, Cyclidiopsis, Euglena, Euglenopsis, Hyalophacus, Khawkinea, Lepocinclis, Phacus, Strombomonas* or *Trachelomonas*, such as the genera and species *Euglena acus, Euglena geniculata, Euglena gracilis, Euglena mixocylindracea, Euglena rostrifera, Euglena viridis, Colacium stentorium, Trachelomonas cylindrica* or *Trachelomonas volvocina*. The nucleic acids used are advantageously derived from algae of the genera *Euglena, Mantoniella* or *Ostreococcus*.

Further advantageous plants are algae such as *Isochrysis* or *Crypthecodinium*, algae/diatoms such as *Thalassiosira* or *Phaeodactylum*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as Shewanella, yeasts or animals such as nematodes such as *Caenorhabditis*, insects, frogs, abalone, or fish. The isolated nucleic acid sequences according to the invention are advantageously derived from an animal of the order of the vertebrates. Preferably, the nucleic acid sequences are derived from the classes of the Vertebrata; *Euteleostomi, Actinopterygii; Neopterygii; Teleostei; Euteleostei, Protacanthopterygii, Salmoniformes; Salmonidae* or *Oncorhynchus* or *Vertebrata, Amphibia, Anura, Pipidae, Xenopus* or *Evertebrata* such as *Protochordata, Tunicata, Holothuroidea, Cionidae* such as *Amaroucium constellatum, Botryllus schlosseri, Ciona intestinalis, Molgula citrina, Molgula manhattensis, Perophora viridis* or *Styela partita*. The nucleic acids are especially advantageously derived from fungi, animals, or from plants such as algae or mosses, preferably from the order of the Salmoniformes, such as the family of the Salmonidae, such as the genus *Salmo*, for example from the genera and species *Oncorhynchus mykiss, Trutta trutta* or *Salmo trutta fario*, from algae, such as the genera *Mantoniella* or *Ostreococcus*, or from the diatoms such as the genera *Thalassiosira* or *Phaeodactylum* or from algae such as *Crypthecodinium*.

In a preferred embodiment, the process furthermore comprises the step of obtaining a cell or an intact organism which comprises the nucleic acid sequences used in the process, where the cell and/or the organism is transformed with a nucleic acid sequence according to the invention which encodes the Δ9-elongase, Δ8-desaturase and/or the Δ5-desaturase, a gene construct or a vector as described above, alone or in combination with further nucleic acid sequences which encode proteins of the fatty acid or lipid metabolism. In a further preferred embodiment, this process furthermore comprises the step of obtaining the oils, lipids or free fatty acids from the organism or from the culture. The culture can, for example, take the form of a fermentation culture, for example in the case of the cultivation of microorganisms, such as, for example, *Mortierella, Thalassiosira, Mantoniella, Ostreococcus, Saccharomyces* or *Thraustochytrium*, or a greenhouse- or field-grown culture of a plant. The cell or the organism produced thus is advantageously a cell of an oil-producing organism, such as an oil crop, such as, for example, peanut, oilseed rape, canola, linseed, hemp, peanut, soybean, safflower, hemp, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

For the purposes of the invention, "transgenic" or "recombinant" means with regard to, for example, a nucleic acid sequence, an expression cassette (=gene construct) or a vector comprising the nucleic acid sequence or an organism transformed with the nucleic acid sequences, expression cassettes or vectors according to the invention, all those constructions brought about by recombinant methods in which either
a) the nucleic acid sequence according to the invention, or
b) a genetic control sequence which is operably linked with the nucleic acid sequence according to the invention, for example a promoter, or
c) a) and b)
are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding Δ5-desaturase gene—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic organism or transgenic plant for the purposes of the invention is therefore understood as meaning, as above, that the nucleic acids used in the process are not at their natural locus in the genome of an organism, it being possible for the nucleic acids to be expressed homologously or heterologously. However, as mentioned, transgenic also means that, while the nucleic acids according to the invention are at their natural position in the genome of an organism, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are fungi such as *Mortierella* or *Phytophtora*, mosses such as *Physcomitrella*, algae such as *Mantoniella, Euglena, Crypthecodinium* or *Ostreococcus*, diatoms such as *Thalassiosira* or *Phaeodactylum*, or plants such as the oil crops.

Organisms or host organisms for the nucleic acids, the expression cassette or the vector used in the process according to the invention are, in principle, advantageously all organisms which are capable of synthesizing fatty acids, specifically unsaturated fatty acids, and/or which are suitable for the expression of recombinant genes. Examples which may be mentioned are plants such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia, Phytophtora* or *Pythium*, bacteria, such as the genus *Escherichia* or *Shewanella*, yeasts, such as the genus *Saccharomyces*, cyanobacteria, ciliates, algae such as *Mantoniella, Euglena, Thalassiosira* or *Ostreococcus*, or protozoans such as dinoflagellates, such as *Crypthecodinium*. Preferred organisms are those which are naturally capable of synthesizing substantial amounts of oil, such as fungi, such as *Mortierella alpina, Pythium insidiosum, Phytophtora infestans*, or plants such as soybean, oilseed rape, coconut, oil palm, safflower, flax, hemp, castor-oil plant, *Calendula*, peanut, cacao bean or sunflower, or yeasts such as *Saccharomyces cerevisiae* with soybean, flax, oilseed rape, safflower, sunflower, *Calendula, Mortierella* or *Saccharomyces cerevisiae* being especially preferred. In principle, host organisms are, in addition to the abovementioned transgenic organisms, also transgenic animals, advantageously nonhuman animals, for example *C. elegans, Ciona intestinalis* or *Xenopus laevis*.

Further utilizable host cells are detailed in: Goeddel, Gene Expression Technology: Methods in Enzymology 185, Academic Press, San Diego, Calif. (1990).

Expression strains which can be used, for example those with a lower protease activity, are described in: Gottesman, S., Gene Expression Technology: Methods in Enzymology 185, Academic Press, San Diego, Calif. (1990) 119-128.

These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvents such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using filler's earth or active charcoal. At the end, the product is deodorized, for example using steam.

The fatty acids produced by the processes of the present invention can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids of formula I or fractions thereof which have been produced by the above-described process, especially preferably oil, lipid or a fatty acid composition comprising a compound of formula I and being derived from transgenic plants.

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmacologicals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid.

The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The ARA produced in the process may be, as described above, in the form of fatty acid derivatives, for example sphingolipids, phosphoglycerides, lipids, glycolipids, phospholipids, monoacylglycerol, diacylglycerol, triacylglycerol or other fatty acid esters.

The ARA and other polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparaliel seed-specific expression of genes.

If microorganisms such as yeasts, such as *Saccharomyces* or *Schizosaccharomyces*, fungi such as *Mortierella, Aspergillus, Phytophtora, Entomophthora, Mucor* or *Thraustochytrium*, algae such as *Isochrysis, Mantoniella, Euglena, Ostreococcus, Phaeodactylum* or *Crypthecodinium* are used as organisms in the process according to the invention, these organisms are advantageously grown in fermentation cultures.

If microorganisms are used as organisms in the process according to the invention, they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while passing in oxygen. The pH of the liquid medium can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview over known cultivation methods can be found in the textbook by Chmiel (Bioprozeβtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must suitably meet the requirements of the strains in question. Descriptions of culture media for various microorganisms can be found in the textbook "Manual of Methods für General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° to 40° C. and preferably 25° C. to 40° C. The culture is continued until formation of the desired product is at a maximum. This aim is normally achieved within 10 to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The fatty acids obtained in the process are also suitable as starting material for the chemical synthesis of further products of interest. For example, they can be used in combination with one another or alone for the preparation of pharmaceuticals, foodstuffs, animal feeds or cosmetics.

All of the nucleic acid sequences used in the process according to the invention are advantageously derived from a eukaryotic organism such as a plant, a microorganism or an animal. The nucleic acid sequences are preferably derived from the order Salmoniformes, algae such as *Mantoniella, Crypthecodinium, Euglena* or *Ostreococcus*, fungi such as the genus *Phytophthora* or from diatoms such as the genera *Thalassiosira* or *Phaeodactylum*.

The invention will now be described in greater detail with reference to the following Examples.

Example 1

Cloning of a FAE1 Elongase from *Perkinsus marinus*

*Perkinsus marinusi* is an oyster protozoan parasite capable of synthesizing saturated and unsaturated fatty acids including the essential fatty acid, arachidonic acid [20:4(n-6)]. *P. marinus* employs the delta-8 (Δ-8) desaturase pathway to synthesize arachidonic acid.
Materials and Methods.
Growth and Harvesting of *P. marinus*.

*Perkinsus marinus* meronts were cultivated at 28° C. in a medium prepared as described by La Peyre et al. (J Eukaryot Microbiol 1993; 40:304-10) and contained amino acids, nucleotides, carbohydrates, and vitamins, but no fetal bovine serum.
Nucleic Acid Manipulation and PCR-Based Cloning.

DNA was extracted from cells using a DNeasy DNA mini kit (Qiagen). DNA were amplified with primers specific to delta5 desaturase gene as follows: the reactions were heated to 95 C for 2 min followed by 35 cycles at 95 C for 1 min, 2 min at 52 and 72 C for 4 min, then a single step at 72 C for 5 min. PCR amplification products were cloned into TOPO vector (Invitrogen) and verified by sequencing. FAE elongase gen was amplified with gene-specific primers (TableI) designed to the 5' and 3' ends of the coding region, with restriction sites to facilitate cloning into the yeast vector (Table I). Forward primers for cloning into yeast expression vector pYES2 (Invitrogen) were designed to contain a G/A at position −3 and a G at position +4 to improve translation initiation in eukaryotic cells.

Oligonucleotide Primers Used in this Study.

Transcripts of *Perkinsus marinus* were analyzed by reverse transcriptase PCR(RT-PCR). Total RNA was extracted from cells using an RNeasy plant mini kit (Qiagen). First strand cDNA was synthesised from total RNA using the SMART RACE cDNA Amplification kit (BD-Clontech, Basingstoke, UK) according to the manufacture's instructions. Single-stranded cDNAs were amplified with following primers.

FAEoperon forward 5'-GGAATTCGAGGAGTAGGATCT-TATCTGAGGATAGTCACACTAGTCGTACT-3' (SEQ ID NO: 11)

FAEoperon reverse 5'-CATCTGCGAATACTAACCATA-CATT (SEQ ID NO: 12)

The reactions were heated to 95 C for 2 min followed by 30 cycles at 94 C for 30 s, 30 at temperatures ranging from 55 to 72 according to the primer design and 72 C for 2 min, then a single step at 72 C for 10 min. PCR amplification products were cloned into TOPO vector (Invitrogen) and verified by sequencing. Surprisingly it was shown that the transcripts of the Δ9-elongase, Δ8-desaturase and Δ5-desaturase are all found on the same mRNA. This is the first example showing PUFA genes to be organized in an operon-like structure.

In a further investigation the specificity of the Δ9-elongase was analyzed. For this purpose the coding sequence of this gene was amplified by RT-PCR as described above using following primers.

Elo2For: 5'-ATGCAAGTTCCCGCGGAGCATCACTCC-3' (SEQ ID NO: 5)

Elo2Rev: 5'-CGTTACGCATCAATATTATGCATAGC-CAACC-3' (SEQ ID NO: 6)

The amplified PCR product was then cloned into a pCR-script vector according to manufacture's recommendations (Stratagen). In a second PCR step the modified sequences for yeast expression were introduced using following primers.

Yeast Expression.

Kpn Elo2For 5'-TTGGTACCATGGGATTTCCTGCGGAG-3' (SEQ ID NO: 7)

Sac Elo1Rev 5'-GGGAGCTCTTACGCATCAATATTATG-CATAGC-3' (SEQ ID NO:

Sequence of the primers is given in the 5' to 3' orientation Restriction sites used for cloning are in bold.

Results

Isolation of FAE1 Elongase from *P. marinus*.

Using publicly available data derived from an *P. marinus* genome sequencing project carried out by TIGR (tigr.org/tdb/e2k1/pmg/), we identified one contig (1047306867) which showed significant homology to known elongases, with the target sequence (designated Elo1For, SEQ ID NO: 9) consisting of an open reading frame of 511 residues and no introns. The putative amino acid derived from the target sequence is SEQ ID NO: 10.

Functional Characterisation in *Saccharomyces cerevisiae*.

The full-length cDNA corresponding to putative Δ9 fatty acid elongase (SEQ ID NO: 9) was cloned into yeast expression vector pYES2 to give a construct designated pYPmFAE. *S. cerevisiae* strain W303-1A was transformed with the pYPmFAE or the empty vector as a control. Transformed cell were grown in a minimal medium containing raffinose and induced with 2% galactose. After 48 h of growth total yeast fatty acids were extracted and the resulting FAMEs analysed by GC.

GC analysis (FIG. 2) revealed that yeast cells transformed with pYPmFAE produced an additional fatty acid, which was identified as eicosadienoic acid indicating that the gene we had cloned encoded a delta 9 fatty acid elongase. Yeast cells expressing the *P. marinus* delta 9 fatty acid elongase is capable of recognizing C18:2 (c9,12) substrate with a 8.2% percentage of conversion rate.

Table 1 shows the fatty acid content of the yeast cells after transformation with pYPmFAE (+) or with the empty vector pYES2 (−) and induction with 2% galactose. The percentage conversion for $18:2^{\Delta 9,12}$ to $20:2^{\Delta 11,14}$, for example is calculated by the equation:

$$\% \text{ conversion} = \frac{[20:2^{\Delta 11,14}]}{[18:2^{\Delta 9,12}] + [20:2^{\Delta 11,14}]}$$

TABLE 1

| % | FATTY ACIDS | | | | | | | | | | % conv |
|---|---|---|---|---|---|---|---|---|---|---|---|
| | 16:0 | $16:1^{\Delta 9}$ | 18:0 | $18:1^{\Delta 9}$ | $18:2^{\Delta 9,12}$ | $20:2^{\Delta 11,14}$ | $18:3^{\Delta 6,9,12}$ | $20:3^{\Delta 8,11,14}$ | $20:4^{\Delta 5,8,11,14}$ | $22:4^{\Delta 7,10,13,18}$ | |
| FAE 18:2+ | 19.05 | 22.79 | 5.15 | 12.54 | 37.14 | 3.33 | 0.00 | 0.00 | 0.00 | 0.00 | 8.2 |
| FAE 18:2− | 20.81 | 19.50 | 5.50 | 12.11 | 42.07 | 0.00 | 0.00 | 0.00 | 0.00 | 0.00 | 0.0 |
| FAE 18:3+ | 18.86 | 19.77 | 4.81 | 11.15 | 0.00 | 0.00 | 44.93 | 0.48 | 0.00 | 0.00 | 1.1 |
| FAE 18:3− | 20.35 | 18.15 | 4.84 | 10.33 | 0.00 | 0.00 | 46.27 | 0.07 | 0.00 | 0.00 | 0.1 |
| FAE 20:4+ | 20.84 | 31.09 | 5.48 | 15.91 | 0.00 | 0.00 | 0.00 | 0.00 | 26.68 | 0.00 | 0.0 |
| FAE 20:4− | 22.13 | 31.00 | 4.55 | 14.65 | 0.00 | 0.00 | 0.00 | 0.00 | 27.67 | 0.00 | 0.0 |

The results presented in Table 1 show that no elongase activity was detected with $20:4^{\Delta 5,8,11,14}$, and a minimal activity (1% conversion) for $18:3^{\Delta 6,9,12}$. It therefore appears that the Δ9 fatty acid elongase is selective for linoleic acid and does not act to elongate other PUFAs.

The invention claimed is:

1. An isolated nucleic acid molecule which encodes a polypeptide with Δ9-elongase activity and which is selected from the group consisting of:
   a) a nucleic acid sequence comprising nucleic acid residues 7668 to 9200 of SEQ ID NO: 1 or the nucleic acid sequence of SEQ ID NO: 9;
   b) a nucleic acid sequence which encodes a polypeptide with Δ9-elongase activity, wherein the polypeptide comprises the amino acid sequence of SEQ ID NO: 2 or SEQ ID NO: 10; and
   c) a derivative of a nucleic acid sequence comprising nucleic acid residues 7668 to 9200 of SEQ ID NO: 1 or the nucleic acid sequence of SEQ ID NO: 9 which encodes a polypeptide with at least 95% identity at the amino acid level with the amino acid sequence of SEQ ID NO: 2 or SEQ ID NO: 10; wherein said polypeptide has Δ9-elongase activity.

2. A gene construct comprising the nucleic acid molecule of claim 1 operably linked with one or more regulatory sequences.

3. A vector comprising the nucleic acid molecule of claim 1 or a gene construct comprising said nucleic acid molecule operably linked with one or more regulatory sequences.

4. A transgenic organism comprising at least one nucleic acid molecule of claim 1, a gene construct comprising said nucleic acid molecule operably linked with one or more regulatory sequences, or a vector comprising said nucleic acid molecule or said gene construct, wherein the organism is a microorganism, yeast, or a plant.

5. The transgenic non human organism of claim 4, wherein the organism is selected from the group consisting of peanut, oilseed rape, canola, sunflower, safflower, poppy, mustard, hemp, castor-oil plant, olive, Calendula, Punica, evening primrose, pumpkin/squash, linseed, soybean, borage, oil palm, coconut and yeast.

6. The transgenic organism of claim 4, wherein the organism is a plant.

7. A process for the conversion of $18:2^{\Delta 9,12}$ (linoleic acid) to $20:2^{\Delta 11,14}$ comprising introducing into an organism which comprises linoleic acid at least one nucleic acid molecule which encodes a polypeptide having Δ9-elongase activity and which comprises:
   a) a nucleic acid sequence comprising nucleic acid residues 7668 to 9200 of SEQ ID NO: 1 or the nucleic acid sequence of SEQ ID NO: 9;
   b) a nucleic acid sequence which encodes a polypeptide with Δ9-elongase activity, wherein the polypeptide comprises the amino acid sequence of SEQ ID NO: 2 or SEQ ID NO:10; or
   c) a derivative of a sequence comprising nucleic acid residues 7668 to 9200 of SEQ ID NO: 1 or the nucleic acid sequence of SEQ ID NO: 9 which encodes a polypeptide with at least 95% identity at the amino acid level with the amino acid sequence of SEQ ID NO: 2 or SEQ ID NO: 10; wherein said polypeptide has Δ9-elongase activity, and expressing said nucleic acid molecule, wherein the organism is a microorganism, yeast, or a plant.

8. The process of claim 7, further including the step of induction with galactose.

9. The process of claim 7, wherein the organism is selected from the group consisting of peanut, oilseed rape, canola, sunflower safflower, poppy, mustard, hem castor-oil plant, olive, Calendula, Punica, evening primrose, pumpkin/squash, linseed, soybean, borage, oil palm, coconut and yeast.

10. The process of claim 8, wherein the organism is selected from the group consisting of peanut, oilseed rape, canola, sunflower, safflower, poppy, mustard, hemp, castor-oil plant, olive, Calendula, Punica, evening primrose, pumpkin/squash, linseed, soybean, borage, oil palm, coconut and yeast.

11. The isolated nucleic acid molecule of claim 1, wherein the nucleic acid sequence encodes a polypeptide comprising the amino acid sequence of SEQ ID NO: 2 or SEQ ID NO: 10 and having Δ9-elongase activity.

12. The isolated nucleic acid molecule of claim 1, wherein the nucleic acid sequence comprises nucleic acid residues 7668 to 9200 of SEQ ID NO: 1 or the nucleic acid sequence of SEQ ID NO: 9 and has Δ9-elongase activity.

13. The process of claim 7, wherein the at least one nucleic acid molecule encodes a polypeptide comprising the amino acid sequence of SEQ ID NO: 2 or SEQ ID NO: 10 and having Δ9-elongase activity.

14. The process of claim 7, wherein the at least one nucleic acid molecule comprises nucleic acid residues 7668 to 9200 of SEQ ID NO: 1 or the nucleic acid sequence of SEQ ID NO: 9 and has Δ9-elongase activity.

15. The process of claim 7, wherein the organism is a plant.

16. The process of claim 8, wherein the organism is a plant.

* * * * *

UNITED STATES PATENT AND TRADEMARK OFFICE
CERTIFICATE OF CORRECTION

| | | |
|---|---|---|
| PATENT NO. | : 8,119,861 B2 | Page 1 of 1 |
| APPLICATION NO. | : 12/279560 | |
| DATED | : February 21, 2012 | |
| INVENTOR(S) | : Johnathan A. Napier et al. | |

It is certified that error appears in the above-identified patent and that said Letters Patent is hereby corrected as shown below:

In the Claims:

In Claim 5, in column 75, on line 48, "5. The transgenic non human organism of claim 4, wherein" should read -- 5. The transgenic organism of claim 4, wherein --.

In Claim 9, in column 76, on line 35, "sunflower safflower, poppy, mustard, hem castor-oil plant," should read -- sunflower, safflower, poppy, mustard, hemp, castor-oil plant, --.

Signed and Sealed this
Twenty-ninth Day of May, 2012

David J. Kappos
*Director of the United States Patent and Trademark Office*

SEQUENCE LISTING

<160> NUMBER OF SEQ ID NOS: 12

<210> SEQ ID NO 1
<211> LENGTH: 18342
<212> TYPE: DNA
<213> ORGANISM: Perkinsus marinus
<220> FEATURE:
<221> NAME/KEY: CDS
<222> LOCATION: (7668)..(9200)
<220> FEATURE:
<221> NAME/KEY: CDS
<222> LOCATION: (9351)..(10724)
<220> FEATURE:
<221> NAME/KEY: CDS
<222> LOCATION: (10842)..(12077)

<400> SEQUENCE: 1

```
tctaagacat catacctaca gtggcttcat ctactgtgat ggttatgatg atgacgacga    60
attcagagtt ggaaaaggaa tttgaggtca gcgatggtga gtttctcgag ggctccattg   120
aagttaccgc cgatagtgcc atcgaagatc aattgcttct tctcctgtaa caggaaatga   180
tcatcactcg agtatccaag gaaaactgta tcgcccgggg acgttgatct ctattagctc   240
aggtttcgtg tagagttgag tcattagata aataaattcc atgaagccaa ggtagtgtta   300
cctggagagc cttgattcgc tcctcgatgg tgttctcgga gataagatgg tgactcctca   360
caatctgctg ctgtcctaga cggtggcaac gctgtatggc ctgcttctct acggccgggt   420
tccaccatgg atctatacag gagtatacca ccctacgtgg gccagcgcag tctcaccgag   480
tatgaagacg tgactcgccc tttggaggtt caacccttca ccaccagcgg aaatcgatac   540
cagcaggagg ctgcagtccg acgctggcga ctgatatagc agaccagggt caagatcaca   600
acacagacat ctcccacctc gatgaaagcc cggatgatcc tggtgcgaac ggcgaggggt   660
atcgatccgt ggatgatctg aggacagtag acactcgacg agctactgta cgtattttca   720
tggttaacga taaccgagag atctgcctta cgaaagtgct aatccctctg gctttgaggt   780
ggtattgtga gagctccagc aacttgacaa agcaggagaa taccagcctg aacgaaggag   840
gactcagaga tccaacgcat gttactgctc ccgttgctaa aaatgagact atgctctctc   900
cggcgggcgc tacgagaaga cttgttagac attacgaagt aagagactcc gcggaattga   960
aagtaattgc tccccaataa taccggatcg atgacctcac cctttagcat tgggatcctg  1020
tctacgcatc tccaagactc tggtgatgag ggcatcgatc ttagacgatg atggtatacc  1080
agggccatgc atctcttgca gttgactgat gacgttattc cttcgggata agcttgaaag  1140
agacagtaaa gctctgattt cctctgagcg tggcatcgct gatgtagtag cagcagtctg  1200
agcctaataa ggagaccagt tgatccacga atgcccccca aagacctacc caggactggt  1260
gtagaaccga gctgctctca caaacgggac actgcacgca agcgctcgac aatgagctga  1320
tattcgtact agctgtaccc acacagtccc tacagccttt aatacgtgag agggggaag  1380 cggctagcca acctgtggaa ctcatgaccg cagtccatcc ataccagatc atcttcccca  1440
taccccgtga tgatatcgtc gtcacatacg tcctaccaat acagtgtgcc tcgcgttatg  1500
catcaacacc tacgcatttc ctcattcctt catcgtcacc agaattcacc aaatacttat  1560
ggtttgcagc ctgaaagcat cagtactgtc aaaattaggg agaccaccta ccaatctgag  1620
```

```
cttcatgata agcgagagca cctcaaccat atgctcgccg atttcatttc gtctcagata   1680
gccgcgtatt ctgtcctggt agagttcgaa aagattgtcg tagacctcac ggtcctttgg   1740
tttcatcgaa agtgtatgca gtgcactcgt taattctggt aggcggactt ccatctgctt   1800
ctccgctttc gtgcgcctca gcatgagacg cttgagaacc ctcgtcctga gcagctccaa   1860
cccctccgct ccttcaaacg catcgaagcc gtggctgatg cgaactccat cgtctggtaa   1920
agcaccgcgc caaagggta cctcttgatg ggattggcaa tgaatcgtgt aaagtaaatg   1980
tagtggctaa ttctgggatg cccgcaggcc ttgcagttct ctatggggtg gtccagcaac   2040
acgcagtcac aacccgccca gtcgcacatc ctagcgccct ccggcagaac ccggaggaat   2100
ctatgggcac aacaatgatg aatttcggtc acgactgtca ccttatcagc gaaaaaggt   2160
ctccaacttt gttttggaga ggagttcccg acaggcacca tcggaacctc gaccgcaagg   2220
cacacctgag catcgatgtt gacacgaagg ggacggaccg ggaggattct tacgcggcct   2280
tagcggtcga ggacccggct gccttgatct tgtgggcctc gtctaagact actctctccc   2340
agcgcaaacc atgcaatagc cctgcacggc gcaatcgggt ctccaagtcc gacctgtcag   2400
tccctggaag gaaagaacga tcatcgatac ctgaggagac cccaacagag ccccacctgt   2460
ctcgtcgcta ctgtcctcga cagctgcttg cgctaggcga accctccggg gtttaaccgc   2520
acgcctcaca atctccgctg ccttacgacg ggccccaccc atatcttgcc cacacgatcg   2580
aggcatcccc atagtagccc cttccatcc cacttcgcta ctgctcatgt tggcagtaga   2640
gagtttcggt agaggactgc attgcggtga tggtttctgg taagatcgga ccggtccggt   2700
gacactccac gcattatcat cgacgttctc tttgttccct gccatttcct cagccttgat   2760
acgcttcccc aagcccagca gaggactctc ctccaggcgc cttccgggca gtcctcccct   2820
ctttacgaga ggactataca tcttcctact gacaggtaca gtcggaccat cgagcactgc   2880
tgaactcccg gtcacaccag gtcgtggtag accattactg aagacgagac ccttctgagt   2940
gataggccca acactcgacc gccattcatg tcgatcggag tcccacgagg ctccgttctc   3000
caccttgata taacctagat tgctgcactc cctcagaggg ctgctgggct tcaatcggac   3060
caccataggc tttgcctctt cctccacgga aatgctcgca ccactcggtc ggccgtgacc   3120
aaggacatga tatcggtgct ggtttaaaga cgagctgata ctgccagccg ctgccgagga   3180
gggctccacg agactgtccc ttgtcgtcca ctgttcctcc ttaaaacctc ctgtatgatc   3240
gatacctctc gaagcaacat gcccaccaat agtgcgttgt aaactagcag aaatagagag   3300
gttgatgcgc aacggtcctg tggaagggcc tatgctcggt ctcacggcac cactagagcc   3360
acccacggac ggtcttgagt acggtgtagt tctccaagtc ggcttatagc agttgtctat   3420
ggagtctctg ccctgctcag cttcggccg taatctcttg agcatgtcga ctagatccct   3480
ccgtgctctc tggtcatcat cgacatcctc ctgtttgacg agatggtcct cccgcactct   3540
cgagccggct tgaccagtga agaagtcctt gatcgtctcc atggatcccg gattacgata   3600
ttgctgccga ttagaattaa ccgagacatt agaaccatac gaaggcgctc tgacctccct   3660
cgaacctccg ccgccaaaa ctgaacggtt ctcttcttgg aagagattct tccgcaatga   3720
ctggcctgtc ggaggagccc catcctgatg atggtaggtg gatgatgatg acgatggtgc   3780
gctcggctga tacactggtg cactgggatg ggctcggccg ctggcgtcat aggtccaagt   3840
ggtacgaggc ctcttcgggc acttctcttt atgcgagaag agcagttctg ggagtatctt   3900
gcgcttgcag tagggacacg ccctttttcag ctgatcgagc tcctttctgt actcggcctc   3960
cagagttctg taagtcgtca gaacgatatc atatcctctc aaggacttag cagtgatctt   4020
```

```
agattttcca tggtacagga atattttcac agtgccaggc cgtaggtatc tattgatctc    4080
ggcctcccac tggagcatcg aggtagtggt gcatacgatc agagtggggt tattcctccc    4140
cacaagtttc ttagtaatca acgagaccgt ttgtatggtc ttccccatgc ccatctcatc    4200
agccaatata ccccccttac agtcctcctt ggtctcctgt tcacacatcc aagcgagacc    4260
ttcacgttgg tatcccagca gcggaattat taactgaaaa taaccaagca atcaatcctc    4320
agagtccggg agccgcacgg tcatccgaag cattccttat atattataag cttgccgacc    4380
tgctctggag ggggatactt gagcaccaac tcgggaggta tcttctggac catcctcccc    4440
agctcccgtt tcaccctggc ttcttcagcc ggctgggtat gtgtgggatt gggatcggcg    4500
ttctcgtctc tgatgaacgc gttagggtac attaattggt aaagttggaa ctccacgaaa    4560
tcaattctga aggatcggag acattagttc gacctgtacc aaatgaccta aaactcaagt    4620
ccattcttcc aacgaaaaac ctccgaagat catggcgcct tcggtagtta acatgtcaac    4680
gtagcgtgtg ttgagaaaaa atacaacagc aatacaagat cgaaagccag cctggtagct    4740
aggatttgaa cctgatgtct tctcctgagt agcaattcag attctagtaa tgtctatcat    4800
actccaacac atgggcctct cttttttaccc tataatgatg agcaaatatg caaaaccaca    4860
agggcggcta cttgacccta ccgcgaccat tcgctctcct gtggtatcat ggatcaccat    4920
ctccatgatc tgatcaacag ttcgtcgtga acgatctgca gtagggttga agacgtagtg    4980
atgaagctgg cattcttcaa tctatgcaga tacatcctca atagtaggga acaccagagg    5040
tcaattaaat gccaacaatt tcaccagaaa gctgagaacc tcagtcccac gaagtgcttg    5100
ctagtcatca gaccgagagt taaacgccga gcctattcgg aaaaccgact atgatgagac    5160
tctcatcgtg tcatattgta tgccatcatc ataatctgat ccaatcacgt catggtatca    5220
gatggcgagt gactcgccgc gagtcagtac ctgaaagtgc atcctatttc cacggcgcgc    5280
gcatgctcat cagcctgtct cttggcagtc gtacgcatgc gtcagcctat tgaatgccac    5340
cacagactca agtcaatgac tcttaaccca gagattaacg aaagtccaga gcatatgtgt    5400
ggacctgtga agaggaagca atgatgagag aatactctgt tcgggcctgt ataagaacac    5460
actgaatagc agagtggaaa tgctgagatc actctggcac acacggagtg agtcggttca    5520
ggtcagctac gaattatttt ccatttcacc cagctgtatg cccgagtata acaaatttct    5580
tcactggggc aaatatgcca cgtcaagata tgccaaagtg gggccactat gccacaccaa    5640
gatctgcttg agtatgatat aaattcttg tctggggcaa atatgccaca ccaagatatg    5700
ccaaagtggg gccactatgc cacaccaaga tctgcttgag tatgatataa atttcttgtg    5760
tagggcaaat atgccacgcc aagatatgcc aaagtggggc cactatgcca caccaagttc    5820
tgcttgagca caatgaattt ctggtgtggg actcatatac cacgccaaaa tacgcctaag    5880
cggggtaact atgccacgcc aaaatatgcc agagtagggc aagtatgaca cgccaagata    5940
tgctcaagta aaatgaattt cttcactggg gcaaatatgc catgccaaga tatgcctgag    6000
tataaacaca caatttcttc agtggggcag acatgccaaa ccaagatctg ctcgagtaca    6060
atgaactggt gtgggtcaaa tataccacgt caaaatatgc caaatcgggg taactatgcc    6120
acgtcaacat aggccagagt ggggcaacta ttatgcgtta agatatgctt aagtacaata    6180
tatttcattt tttcactggg acaaatatgc cacgccaaga tgtgtccgag tatgaaaaaa    6240
tcttcagtga gacacctatg ccaggacaag atatatcgga gaacaataaa tttcgtaagt    6300
gggataaata tgccacgccg agatataccct gagtggggca aatatgccaa gccgagatat    6360
gctcgagtac agtgaacttc ttcagtaggg ctgatatgcc cgccaaaaca tgcctgggtg    6420
```

```
tacgaaatta ttcagtgaaa caaatttcct cagtgggggtt acccacttat cttggcgtgc    6480
cataggtagc ccactggggt aaccatgcca cgccaagata tgcccgagta caacaaaatt    6540
attcggtgag gcagatatac cacccccgata catcactgaa acaacaaat ttcgccagtg    6600 gggcagctat gccatcccaa gaaatgcccc agtacacgca atctcccgag agcgcgacct    6660
agggcatcca ccttggtcgg aaaaacaaac gaaacacaat ccggcttgga cgaattgcgg    6720
aagataaatg cgcatagtaa agtcgactcc gttcgagagt agacatgcca tttccgagct    6780
taactgcgac atgctatctt ctcaggagag actctgacga gtatttcctt ggtaatttcc    6840
agtggagagt ggacactgaa cacagacctc tgaccccgcg cagtactcac aagatgacgc    6900
tccgactgag aaaagattga tcttactaac tgtgaagcag acatacgaaa ggtgtattcc    6960
aatcttgctg ttgttgttat tgttgtgagt ctccgtgtgg gagtgaaccg catcccattg    7020
tcgagtgaat cgagcggcgc accgaaagat gagcaatact cagactgatg tgcatgagtg    7080
caccatagaa atacgaaaca gcgtgatagt atcagcattt tcctgcctgt ctgattcggg    7140
atttgtggac atgcaccatc cagcattctc cagaggggag cggcacgcat ggcaaaattg    7200
tcaaattcaa tactattgag agcaccaaat caattcgagt ggtcgcgcat tagcgtaact    7260
ctaatatgcg atcaacccca ataacccctc ggcgcgtcta tacgggccct caaatactgg    7320
tgagatgcaa aatcaagcag tttaggtcgg aaattgtcgt ggttcgtcaa aactcaattc    7380
atcgagtccc tccggtcatt cgtcgcgcgc gttgaagacg aacggcgcac caatcatttg    7440
cgcacgcgtg caaaacgctc attgcgcagg cctacattcc agaatgtagg gccacggtat    7500
gtgctgcact aacatcgcca gactctacac tcgtagcata atatatggaa ttcgaggagt    7560
aggatcttat ctgaggatag tcacactagt cgtactgctg aatcagcgtt gctgattctg    7620
caacgttatg actattaaga cgatcgttag gacgtcatta cgtcgtc atg caa gtt     7676
                                                    Met Gln Val
                                                      1 ccc gcg gag cat cac tcc act cgg gtt ata tct atc tgt gat atc gtc      7724
Pro Ala Glu His His Ser Thr Arg Val Ile Ser Ile Cys Asp Ile Val
  5                  10                  15 atc tca ggc ccc ttt gga atg tgt aac cat gat tac tcc gct tct ata      7772
Ile Ser Gly Pro Phe Gly Met Cys Asn His Asp Tyr Ser Ala Ser Ile
 20                  25                  30                  35 cct gcc tct agt agt ggt agc act cga cgt atg cgt ttg gta gcc tac      7820
Pro Ala Ser Ser Ser Gly Ser Thr Arg Arg Met Arg Leu Val Ala Tyr
                 40                  45                  50 atc aca ttg gtc tct atc cac tat caa cag cta ctc ttt tac tct tct      7868
Ile Thr Leu Val Ser Ile His Tyr Gln Gln Leu Leu Phe Tyr Ser Ser
         55                  60                  65 atc ata act ata atc act ggc tat cac tac tat gtc gca gct ctg ccc      7916
Ile Ile Thr Ile Ile Thr Gly Tyr His Tyr Tyr Val Ala Ala Leu Pro
             70                  75                  80 ctt tac gac atc tca att gct cta tct gtg ctt tcg gga cta aca cta      7964
Leu Tyr Asp Ile Ser Ile Ala Leu Ser Val Leu Ser Gly Leu Thr Leu
 85                  90                  95 ctg tgg tta tgt aat tgc tat tac aac agc aag ccc aat gta ttc tgc      8012
Leu Trp Leu Cys Asn Cys Tyr Tyr Asn Ser Lys Pro Asn Val Phe Cys
100                 105                 110                 115 atc gat cat gtt gag ttt gac gct cct ccc tct tgg aag gtc agt cat      8060
Ile Asp His Val Glu Phe Asp Ala Pro Pro Ser Trp Lys Val Ser His
                120                 125                 130 gaa gac atc atc aac att gcc aag ata caa ggt tgc tac acg gaa gat      8108
Glu Asp Ile Ile Asn Ile Ala Lys Ile Gln Gly Cys Tyr Thr Glu Asp
                135                 140                 145
```

```
tca ctc aac ttc atg cag cgt ctt ctc gag agg tct ggt act tgc cct    8156
Ser Leu Asn Phe Met Gln Arg Leu Leu Glu Arg Ser Gly Thr Cys Pro
        150                 155                 160 gat aag agt gct gct tac cct cca gtg gtt gtt gag tca ctg agg act    8204
Asp Lys Ser Ala Ala Tyr Pro Pro Val Val Val Glu Ser Leu Arg Thr
165                 170                 175 aac gcc ccc gcc gat gcc tct gct gtc aat act aga gag gaa gcg agg    8252
Asn Ala Pro Ala Asp Ala Ser Ala Val Asn Thr Arg Glu Glu Ala Arg
180                 185                 190                 195 gaa gtg atc ata act acg gtc aaa gat ctg ctc aag aaa act ggt gtg    8300
Glu Val Ile Ile Thr Thr Val Lys Asp Leu Leu Lys Lys Thr Gly Val
                200                 205                 210 cat cct aaa tct atc gac tac atc atc gtc aat tgc gcc atg tac aac    8348
His Pro Lys Ser Ile Asp Tyr Ile Ile Val Asn Cys Ala Met Tyr Asn
            215                 220                 225 ccg aca ccg tca cat gct gct atg ata gtg aat gaa gtc ggt atg agg    8396
Pro Thr Pro Ser His Ala Ala Met Ile Val Asn Glu Val Gly Met Arg
        230                 235                 240 aat gac gtt atc acc tat aac ctc agt ggt atg ggg tgt agt gcc ggt    8444
Asn Asp Val Ile Thr Tyr Asn Leu Ser Gly Met Gly Cys Ser Ala Gly
245                 250                 255 gtt atc aca att gat cta gca acg cgt ctg ttg aga gag acc aga ggt    8492
Val Ile Thr Ile Asp Leu Ala Thr Arg Leu Leu Arg Glu Thr Arg Gly
260                 265                 270                 275 agg gca ctg att gtc tca act gag ata cta act cgt tgc ttc tat cgt    8540
Arg Ala Leu Ile Val Ser Thr Glu Ile Leu Thr Arg Cys Phe Tyr Arg
                280                 285                 290 ggt aat gat cgt gaa cca ctg atg ggt aac aca tta ttc aga tgt ggt    8588
Gly Asn Asp Arg Glu Pro Leu Met Gly Asn Thr Leu Phe Arg Cys Gly
            295                 300                 305 ggt gct gct gct ttg cta tcg tca ttg cct aaa gac cta tct cgt gcc    8636
Gly Ala Ala Ala Leu Leu Ser Ser Leu Pro Lys Asp Leu Ser Arg Ala
        310                 315                 320 aaa tat aag ttg tta cat acc gta aga acg caa gtt ctc ggt aat gag    8684
Lys Tyr Lys Leu Leu His Thr Val Arg Thr Gln Val Leu Gly Asn Glu
325                 330                 335 agt ttt gaa acg att atg gag act gat gac agt acc aag ccc aac agt    8732
Ser Phe Glu Thr Ile Met Glu Thr Asp Asp Ser Thr Lys Pro Asn Ser
340                 345                 350                 355 att gtt aca cta agg ctc cag aag agc atc atc aaa gtt gct gct gtt    8780
Ile Val Thr Leu Arg Leu Gln Lys Ser Ile Ile Lys Val Ala Ala Val
                360                 365                 370 gct att aaa caa aat ttt act aag ctt gct tat atg gtt ctc cct ctg    8828
Ala Ile Lys Gln Asn Phe Thr Lys Leu Ala Tyr Met Val Leu Pro Leu
            375                 380                 385 aga gaa ctg ttg aag gtc tta tac tcg atg gtg acg atg aaa atg aga    8876
Arg Glu Leu Leu Lys Val Leu Tyr Ser Met Val Thr Met Lys Met Arg
        390                 395                 400 aga aag tcg tca aaa gaa ggt cgc gag ttg tac gta cct gat ttt aga    8924
Arg Lys Ser Ser Lys Glu Gly Arg Glu Leu Tyr Val Pro Asp Phe Arg
405                 410                 415 aag ggt act gat cat tgg tgt att cat gct ggt ggc cgt ggt gta ttg    8972
Lys Gly Thr Asp His Trp Cys Ile His Ala Gly Gly Arg Gly Val Leu
420                 425                 430                 435 gat acc tta caa gat tct ctc cag ctg tca gac tac gat atc caa gca    9020
Asp Thr Leu Gln Asp Ser Leu Gln Leu Ser Asp Tyr Asp Ile Gln Ala
                440                 445                 450 agc cgt agt gtt ctc tat gag aga ggc aac acc agt agc agc agc ata    9068
Ser Arg Ser Val Leu Tyr Glu Arg Gly Asn Thr Ser Ser Ser Ser Ile
            455                 460                 465
```

```
tgg tat gag ttg gca tgg ctc gaa cgt gac caa cgt att aag cgt gga    9116
Trp Tyr Glu Leu Ala Trp Leu Glu Arg Asp Gln Arg Ile Lys Arg Gly
        470             475             480 gat agg gta tta cag ttg gct ttt ggt agt ggt ttc aaa tgt aac tca    9164
Asp Arg Val Leu Gln Leu Ala Phe Gly Ser Gly Phe Lys Cys Asn Ser
485             490             495 tca gta tgg ttg gct atg cat aat att gat gcg taa cgacaatcag         9210
Ser Val Trp Leu Ala Met His Asn Ile Asp Ala
500             505             510 tttttctcac tatgagttgg ctccaccgta atcaatggcc atcatctcct tttctagtta  9270
ttatcgatga ttatagtcag tgccgatgtg tgctagtgtt ttactcttta tcaacttgtg  9330
agtttcaggc ccctttccc atg act act tca acc act act gtg caa cta caa  9383
                     Met Thr Thr Ser Thr Thr Thr Val Gln Leu Gln
                                     515             520 gaa gac ctg tca agt ggt gac cag aac gcc cac ccc agt cca agc cga    9431
Glu Asp Leu Ser Ser Gly Asp Gln Asn Ala His Pro Ser Pro Ser Arg
        525             530             535 gct act cct agt gtt ggt gat act aag gag gat gcg agg gtt gtg atc    9479
Ala Thr Pro Ser Val Gly Asp Thr Lys Glu Asp Ala Arg Val Val Ile
            540             545             550 aaa cta ttt ggt aca tgg gtt gat gtt aca gct tgg ttg aat gac cat    9527
Lys Leu Phe Gly Thr Trp Val Asp Val Thr Ala Trp Leu Asn Asp His
555             560             565 cct ggt ggt tct aaa gtg ctc aga gca ttc aac aag aag gac gcg act    9575
Pro Gly Gly Ser Lys Val Leu Arg Ala Phe Asn Lys Lys Asp Ala Thr
570             575             580             585 gat gct gtt atg gcc atg cac act gat gaa gct atc aag cgc atc atc    9623
Asp Ala Val Met Ala Met His Thr Asp Glu Ala Ile Lys Arg Ile Ile
            590             595             600 aga ttt tca aat gtg gtc tcc tcg gcc ccc atc aac gcc tct att ggt    9671
Arg Phe Ser Asn Val Val Ser Ser Ala Pro Ile Asn Ala Ser Ile Gly
            605             610             615 gat gtc cag gtt att gag aaa tct cta tcg aga gaa cag ttg atg tat    9719
Asp Val Gln Val Ile Glu Lys Ser Leu Ser Arg Glu Gln Leu Met Tyr
            620             625             630 tac aag ctc cgc act ctt gct aga aac cag ggc tgg ttt caa agc aat    9767
Tyr Lys Leu Arg Thr Leu Ala Arg Asn Gln Gly Trp Phe Gln Ser Asn
635             640             645 cta tta tat gaa gga gtg aaa gca atg ata gcc ttc ggt ttg ctc atc    9815
Leu Leu Tyr Glu Gly Val Lys Ala Met Ile Ala Phe Gly Leu Leu Ile
650             655             660             665 atc ggg ttt gct act ctc tac ttt gac tat ggt att tgg tca acc gca    9863
Ile Gly Phe Ala Thr Leu Tyr Phe Asp Tyr Gly Ile Trp Ser Thr Ala
            670             675             680 ctg ata ggt ttc gct tgg ttt cag ctg ggg tgg ttg gga cat gac tgg    9911
Leu Ile Gly Phe Ala Trp Phe Gln Leu Gly Trp Leu Gly His Asp Trp
            685             690             695 tca cat cat aca gct cta cct aag tct act act aac tgt gcg aac tac    9959
Ser His His Thr Ala Leu Pro Lys Ser Thr Thr Asn Cys Ala Asn Tyr
            700             705             710 aac gac tat ctt ggc tgg ctt acc ggt ttg gcc aga ggg aat aca ctt    10007
Asn Asp Tyr Leu Gly Trp Leu Thr Gly Leu Ala Arg Gly Asn Thr Leu
715             720             725 ctg tgg tgg aaa ctg agg cac aat act cat cac gtg ctg acc aat cag    10055
Leu Trp Trp Lys Leu Arg His Asn Thr His His Val Leu Thr Asn Gln
730             735             740             745 tac gag aat gat cct gat att cta act caa cca ccg ttg cat ttt ttc    10103
Tyr Glu Asn Asp Pro Asp Ile Leu Thr Gln Pro Pro Leu His Phe Phe
                750             755             760
```

```
gag gac ttc gat gtt ggt aat gtg aac aga tat caa gct gtc tac tac    10151
Glu Asp Phe Asp Val Gly Asn Val Asn Arg Tyr Gln Ala Val Tyr Tyr
            765                 770                 775 cta cca atg tta act cta ctg cat cta ttt tgg tta tac gag tcg gta    10199
Leu Pro Met Leu Thr Leu Leu His Leu Phe Trp Leu Tyr Glu Ser Val
        780                 785                 790 ttg gtt tgc ttg aga caa agt agg tct att aat aga tac aac cgt atg    10247
Leu Val Cys Leu Arg Gln Ser Arg Ser Ile Asn Arg Tyr Asn Arg Met
    795                 800                 805 cat gcc agg agg gat acc gta gct ttg gta ctt cac ata ctc att gtt    10295
His Ala Arg Arg Asp Thr Val Ala Leu Val Leu His Ile Leu Ile Val
810                 815                 820                 825 ggc atc ata tcg tac acc agt ggt aag tat ttg ctc atc ctt ctg gcc    10343
Gly Ile Ile Ser Tyr Thr Ser Gly Lys Tyr Leu Leu Ile Leu Leu Ala
                830                 835                 840 tac atg ctt agt ggc ttt cta act gct gtt gtt gta ttt gcc agc cac    10391
Tyr Met Leu Ser Gly Phe Leu Thr Ala Val Val Val Phe Ala Ser His
            845                 850                 855 tac aac gag cct agg gta gct tct ggt gaa tcc tta tca ctc gtt cgt    10439
Tyr Asn Glu Pro Arg Val Ala Ser Gly Glu Ser Leu Ser Leu Val Arg
        860                 865                 870 cag aca ttg tta acc act atc aat ata ggc tca ttc agt gat act cat    10487
Gln Thr Leu Leu Thr Thr Ile Asn Ile Gly Ser Phe Ser Asp Thr His
    875                 880                 885 tgg gag aag aag ttg tgg ttc tat cta act ggt ggt ctt aat atg caa    10535
Trp Glu Lys Lys Leu Trp Phe Tyr Leu Thr Gly Gly Leu Asn Met Gln
890                 895                 900                 905 atc gag cat cat ctc ttc cca aca atg ccc cgc cat aat ctt ccg aag    10583
Ile Glu His His Leu Phe Pro Thr Met Pro Arg His Asn Leu Pro Lys
                910                 915                 920 aca act ttt ctg gtc aag tca cta gcc cag gag cta gga ctg cca tac    10631
Thr Thr Phe Leu Val Lys Ser Leu Ala Gln Glu Leu Gly Leu Pro Tyr
            925                 930                 935 aag gaa acc aac att gtc agt tta acc aag gcg gcc gtt act act ttg    10679
Lys Glu Thr Asn Ile Val Ser Leu Thr Lys Ala Ala Val Thr Thr Leu
        940                 945                 950 cat cat aat gct ctg cgt aac atc gag aga ttg ctt gct agg tag        10724
His His Asn Ala Leu Arg Asn Ile Glu Arg Leu Leu Ala Arg
    955                 960                 965 ttctcatcat tgcaaccgca acaagaacat ggtcaactcg tagtggtggt agaggattgt   10784
cgtcatggtc agtagctttc tgatagaatc ttttcatct tcttcctgtt gtgttga      10841 atg tct tct ctt acc ctc tac aga ggc ccc ttt tcc cga atg gtg ctc    10889
Met Ser Ser Leu Thr Leu Tyr Arg Gly Pro Phe Ser Arg Met Val Leu
            970                 975                 980 cct cgt cag gaa atc tgc atc aat ggt cgc ata tac gat gtc act gag    10937
Pro Arg Gln Glu Ile Cys Ile Asn Gly Arg Ile Tyr Asp Val Thr Glu
        985                 990                 995 ttc atc aat cgt cat cca ggt ggt aag att atc ctc ttc caa gtt        10982
Phe Ile Asn Arg His Pro Gly Gly Lys Ile Ile Leu Phe Gln Val
1000                1005                1010 ggt gct gat gcc act gat gct ttt cgt gag ttt cat gct ggc agt        11027
Gly Ala Asp Ala Thr Asp Ala Phe Arg Glu Phe His Ala Gly Ser
1015                1020                1025 gag aag gca gag aag atc ctc aaa acc tac cca tcc cgt gat gat        11072
Glu Lys Ala Glu Lys Ile Leu Lys Thr Tyr Pro Ser Arg Asp Asp
1030                1035                1040 gac ggt act ttc ctt cct tca acc caa cgc tcc atc atg gat gat        11117
Asp Gly Thr Phe Leu Pro Ser Thr Gln Arg Ser Ile Met Asp Asp
1045                1050                1055
```

| | | |
|---|---|---|
| ttc aaa cgc cta aga gat gac ctc gtc agc aga ggt gtc ttc aag<br>Phe Lys Arg Leu Arg Asp Asp Leu Val Ser Arg Gly Val Phe Lys<br>1060                       1065                    1070 | 11162 |
| cca agc gtc atg cat gtt gta tac cgc tgc ttg gaa gtc gtt gct<br>Pro Ser Val Met His Val Val Tyr Arg Cys Leu Glu Val Val Ala<br>1075                       1080                    1085 | 11207 |
| ctc tat ctc att ggc ttc tat ttg gct ctg tgc acc agt aat gtg<br>Leu Tyr Leu Ile Gly Phe Tyr Leu Ala Leu Cys Thr Ser Asn Val<br>1090                       1095                    1100 | 11252 |
| tac gtt ggg tgt gct gta ctt ggt gta gct caa ggt cgt gct ggt<br>Tyr Val Gly Cys Ala Val Leu Gly Val Ala Gln Gly Arg Ala Gly<br>1105                       1110                    1115 | 11297 |
| tgg ttg atg cat gaa gga ggt cat cac tct ctg act ggt aac tgg<br>Trp Leu Met His Glu Gly Gly His His Ser Leu Thr Gly Asn Trp<br>1120                       1125                    1130 | 11342 |
| aaa gtt gac cag ttc ctc caa gaa cta ttt ttc ggc att ggt tgt<br>Lys Val Asp Gln Phe Leu Gln Glu Leu Phe Phe Gly Ile Gly Cys<br>1135                       1140                    1145 | 11387 |
| ggt atg tca gct gcg tgg tgg cgc aat gca cac aac aag cat cac<br>Gly Met Ser Ala Ala Trp Trp Arg Asn Ala His Asn Lys His His<br>1150                       1155                    1160 | 11432 |
| gct gct cct cag cat tta ggg aaa gat gtt gat ctc gag aca ttg<br>Ala Ala Pro Gln His Leu Gly Lys Asp Val Asp Leu Glu Thr Leu<br>1165                       1170                    1175 | 11477 |
| cct ctg gtc gcc ttc aat aag gcc gta ctt cga ggc cgt cta ccg<br>Pro Leu Val Ala Phe Asn Lys Ala Val Leu Arg Gly Arg Leu Pro<br>1180                       1185                    1190 | 11522 |
| tct gtc tgg atc aga tca caa gct gtg tgc ttt gca ccg ata tca<br>Ser Val Trp Ile Arg Ser Gln Ala Val Cys Phe Ala Pro Ile Ser<br>1195                       1200                    1205 | 11567 |
| aca cta ctg gta tcg ttc ttt tgg caa ttc tac cta cac ccg agg<br>Thr Leu Leu Val Ser Phe Phe Trp Gln Phe Tyr Leu His Pro Arg<br>1210                       1215                    1220 | 11612 |
| cat att att agg aca ggt cga cga atg gag tct ttc tgg cta ctc<br>His Ile Ile Arg Thr Gly Arg Arg Met Glu Ser Phe Trp Leu Leu<br>1225                       1230                    1235 | 11657 |
| gta cgc tac tta gtt att gtg tac ctc ggg ttc agc tat gga ttg<br>Val Arg Tyr Leu Val Ile Val Tyr Leu Gly Phe Ser Tyr Gly Leu<br>1240                       1245                    1250 | 11702 |
| gta tcg gtc ttg tta tgt tac atc gca agt gtg cat gtt ggt ggt<br>Val Ser Val Leu Leu Cys Tyr Ile Ala Ser Val His Val Gly Gly<br>1255                       1260                    1265 | 11747 |
| atg tac atc ttt gta cac ttc gct cta tca cat aca cat tta cct<br>Met Tyr Ile Phe Val His Phe Ala Leu Ser His Thr His Leu Pro<br>1270                       1275                    1280 | 11792 |
| gtc att aac cag cat ggt aga gct aac tgg ttg gaa tac gca tct<br>Val Ile Asn Gln His Gly Arg Ala Asn Trp Leu Glu Tyr Ala Ser<br>1285                       1290                    1295 | 11837 |
| aag cac aca gtt aat gtg tca act aac aat tat ttc gtc aca tgg<br>Lys His Thr Val Asn Val Ser Thr Asn Asn Tyr Phe Val Thr Trp<br>1300                       1305                    1310 | 11882 |
| ctc atg agt tat ttg aat tat caa ata gag cat cat ctc ttc ccg<br>Leu Met Ser Tyr Leu Asn Tyr Gln Ile Glu His His Leu Phe Pro<br>1315                       1320                    1325 | 11927 |
| tca tgt ccc cag ttt aga ttc cct ggt tac gtc agt atg agg gtt<br>Ser Cys Pro Gln Phe Arg Phe Pro Gly Tyr Val Ser Met Arg Val<br>1330                       1335                    1340 | 11972 |
| cga gaa ttt ttt cat aag cat gga ttg aag tat aac gag gtc ggc<br>Arg Glu Phe Phe His Lys His Gly Leu Lys Tyr Asn Glu Val Gly<br>1345                       1350                    1355 | 12017 |

```
tat cta cat gca ctc aat ctc aca ttt tca aat ctg gct gct gtt      12062
Tyr Leu His Ala Leu Asn Leu Thr Phe Ser Asn Leu Ala Ala Val
1360                1365                1370 gcc ata gtg gaa tag ctcaatagtg taggagagca tagtagacgc ttatgattgg   12117
Ala Ile Val Glu
1375 tatgtaaaat caataatgtt tggttgagag tgatcaatgt tttctaccag cggagcacta   12177
ataatctgca gcatatacca taacatatcg aaaactctgc atttcttata gttctcattc   12237
ctagtaagga ccacttcgtc ctagtaatta tcgcccaaca cgggaggagg ttagttcgat   12297
gacaaggttg agtatgcctg ctgcaattac cgtgtctgga ctgaaacgta tcatccctat   12357
cgttacaact cattccccgc actctggtgc ataatatgcg cgattcagca ccctttattt   12417
ctcccccctca acgacccctct cttccgcaca ccgtccttag caggtcaaat ctacccgtca   12477
attatcgtga taccacccctt gagttgccca actaatacaa ctcaactaca ataagtacac   12537
tgcgaatgca tcattaacca tcaacaatat gctcattaaa taataatcta tcatcttcgg   12597
acatctcctg ggtgctctcc tcttcactac cggggccagt ctcaatcgat gaccctacta   12657
tgggcaactc tgacgatgac caagatgtta aaacgtgaag ctgtgaatcc aagcactcac   12717
tcggatcgag aggctcagtt cctctggacc gaactgggct gttcaacatt ccaccagacc   12777
ggctatctct catccatagc agaatgccca cccctatcga tgctgtaccg atgaagaaga   12837
agaacttctc tacggctacg taggagccag tggatgaacc tgtcgccgag accaatgggg   12897
acaggaacag tggagcagta tgtaggcgtg gacctcccat attaatgcgt accatcatat   12957
gagagttttg ctatgcaagg cttacacacg gattcgaata aagtgtaga aaaaccaatg   13017
aaattttccc gattttgctc agaatttcca tattgtcagc aacagatgaa gttgaccatg   13077
tgcattatct tccatacagg gtacagattc tacggttgca ctatacgata acattggggt   13137
gtgatacgac aacactgagc aattgatagg atggaccccc tgagtccggg gccctgagca   13197
aagtgcttag atctagagca cagtattgaa gttgaattta cactgaggat tgcatcacta   13257
tcaagttgcc accatacacc tcgatcagca tttgtccact tacgtatatg agccactata   13317
acaggcgtaa ccgccaagcc gaagttttgt gcagccgttg taacaccata ggccgcgcct   13377
aacagacaaa ccggagtcac aaccatcgat gcagcgatga gtccctggtt ctatccccgg   13437
caacatcatt ttaatgtcga aaactcaagt tctacgatga ttgccaatca cacataatgc   13497
agcttgttaa gagatcaagc cagaaattct ccacagcaac ctaccagtct tcctaggagg   13557
tactgcagct gctaccaacg gccatactgc agaggcgaac accgtatagg atagccccaa   13617
aacggtcata gatatcacct acacaacaac taaacttaga acgaataaag cctcgtaccg   13677
ggtgcaatat aggcaggatg atatgtgcca atgtcgccat agtaaaacta gccagaagaa   13737
aatagaggcg gtaacccaat ttgtctatgc atataccagc gataggagag cccaatgctg   13797
acacccccaaa aagtatctga tcgaatattc tccaactaaa tgatcataat aataacgagc   13857
cattgaaggt cactcgagag cggtatgagt tgcaccgcca tacggtacga aacagtatca   13917
ctatgttgtg ctaatgctca ttccctagca gaatcacaac atagcagaaa agaagggcga   13977
tcagttctgc actgcattcg aattacacag gaatgctctc tacaaaaccg ttatgcaaat   14037
cacctttggtc aatcgagaga gttcatcaat aactcttgag gggcatgacg tcaataatag   14097
tgaaaaacgg ttaacatcat tttactatct actgttgagg gcgacaatat gacaactgta   14157
taggaaaaac tgttagtaat tctatatcct tactcccatg atctgtccaa ctttaacatg   14217
ggcagccgct ttatccatgg ttggatacca cacctcgacg aaaaatgccg cggcgatgtt   14277
```

```
attgaaaggc agtataaccg cataggccag cacgcagctg agacatacca accagaagtc   14337
taccgataat gacaatgacg attggagact gagaaaaaag gaagaacttc aacacagtgg   14397
tgacaatatt tcgccataag tagccgttat aactgcgcat ttctcagtag aaaaaccgaa   14457
aaatcgtgtt gaaaactgac aaacattctt tcgaataaca aagttaaggt atgtgagagc   14517
tccaagccac cactagcatt acttctctat aaagccctga ctgggagctt cctcactagt   14577
gatatcatca tcgatgtgct tcgtgaaata acacaacact aacgttagaa taaccgtgcc   14637
tgaaaaaagt ccaccgatgg tgacaccata actacgagaa cagcttactt gtcaccgcta   14697
taagccccgc tatgaacgct cccgttacct aggaaacata atgtagaaat atatgtgtgg   14757
tttcctcagc tgaggtcgta aggttcctca ctacattatg gaaatccaca aacgattttg   14817
ggtagaagcg tacaaaaacc aacaataagt cctcaaaatt tttccagaat ttccataatt   14877
ttaccaacac atgtagttga ccatgtgtat ccatagatag cgataggttc atctcaaaca   14937
cttactccat atcgtgcctc tacaccaggt gacagcaaat cgttgagaac cgagccaaat   14997
cgggcaactg agaggtttag tcccaatgca aaggcgatct cctgccctcg gaaccagcct   15057
gctagaagag tcgtctgtgc cacctgaaga taaaggtata agaggaaggt caccgagagt   15117
tccccttaca ttcatgctct ccccgcctag tccgtagatt acccttccta gcagcatagt   15177
cctcatagaa aaataatacg acccgacaca ttgtagcgct tgcccgagca ataacagtac   15237
cgccagtagg aggagcatgg aacctgagcag agcttcttga catgctaaaa ggcctacagg   15297
gataaactgc attttaatg ggagccttcg gaatcttact actacatgag acattgaaaa   15357
agtttaggtt tttgcatgga ctttgaagaa ctattccaca cagctacttt aatattcatt   15417
gatcacctct gaaatgttgt acaagtttca caaaattcac tcaagtgccg aagcacatca   15477
tcacatcata acagcatatc aaacgctcgt tacctcatac caatccactc tatagagact   15537
cccagtatta atggcgttac catattgggc agggcataga cggtatataa gagattgaag   15597
tagtaggtat attcctcgac agtcataccg ctccctccac ctaaagtagc tgatgcggtc   15657
acttctgaca caacctacc ggtgaatcga gcctgcagtt gatcgtttat cgcggaggga   15717
atatcatagg cgtagtactg gccagagagc gctagacagg ccacgatgag aacagcccat   15777
cttagttttt caggagggtc gggagtagac ataataaaat catagctacg aaacagaaat   15837
tcagccaagt ttgagaaaat accttcccca ggatttgata acaacaggaa aaatgtttat   15897
aatgtgatga tgttaaactg attaaagaat gtgttcctag ccgtgtagga aattcaaaat   15957
gagtttcact cgggaacatt ctggaagaat cactgcgacg aaagcgatct ggacacagca   16017
acgagcagcg gttgactttt cacccgaaac cctcacgaca gtcccttcgc gaaaatcata   16077
caggcaaagt ttcatgaaaa aaatgcaatt tttcggtaaa aaacccgcga gaaaaaccgt   16137
cagtgatgat tgacgatccg attacaccaa aaatgctgat atttttacgg aaaattttc    16197
cgtaaaagct caggccagcc caggcgtctc gcactgattc atcccttccc ataataacac   16257
aattcctcta ctatggacca atacgagtct tagctgtaaa gggctaccac cagtagcaga   16317
gccaacagta acagtaagaa aatgatcaac catagaagag atgtagacta aacgcatgaa   16377
gtgaggccag ggacagctca acagctactc aatgtgagag tcttgttgaa ttttgccgag   16437
gtaataatcg ataaaatcaa aacaatgctg tttcacccgt tttacgcgaa gtgacgtaaa   16497
actcggtgta aaacgcgata ttcgcgctat gcagtagtcg tgaaatatgt ttttcatcag   16557
tgttttcat atcactaggg gaaactccaa cacattcaca agtagaaagg aacaacaact   16617
gcacaaaacg tcataaacca caccaagttc ggttccgtca aattggtatt acgatcgaac   16677
```

-continued

```
cctctagaat tttcccccac atcatgtcgt cattggctca ctctgcgcca ataatttagc  16737
gcgcgcccga ccgaaaagat ctcagaaata ctcaagccta ccttgcatct gtcgtattaa  16797
tgggcggcac gcttcagacg tgttacgctc cggcagtgag gattatatgc atattttact  16857
tatatttctt atagaatata agaacactga cgtactaaac tatacaaacc atgtgttgtt  16917
ctattttcaa cctcaagcag tctgattgac agatcccgcg ggaaaacaga caaaagaatg  16977
gtaggcggta tctgtacact acacagtgag gggaactttc agagcccgaa aagtatgctt  17037
aggcgtcttc gacccgctgg tgtccagggt tcgcaacgca acaggctggg aactctacac  17097
attttcaatc tcaaattcag cgaatgaaag aacaaattga atagtgaaag ttgatttcca  17157
tagagtgaca ggaattttct tcggctgaaa actcatttag cccatgggaa tcaaatgtga  17217
ttgaaaaagt gtataaaaca accaatatcg acgatcgagg aattatgtat tctccgatat  17277
ttaaatctta taattttttc actcatgaag tttctcgaga gcggtataac caggtaaatg  17337
atatcatgat tgaacctaat acccgggtga acgaccgtat ttcccaaccg tgaatcatcg  17397
atcacatgga ccacaagctc agtgcgtcaa actgatatac gcctactgta ttcacataac  17457
tatagaactt catcaacaca actgctgcat atgtgaaaac ttgaaagtgt cttatcatca  17517
atctatgaaa ggcaggaacg ataacatagt cgcatttcta acgactacga acaatgacgt  17577
ttaatatttt gggaagatca cgatctttac atagtacttg cgcatgagcg acaatgagat  17637
cggtctatcg tacgtaacag acaacaattg cttcgaatcg gtaacatcac cgattgaaga  17697
gttttaacag gagataaacg atgaagattt acagtatagg tagccatcaa acattaataa  17757
cagaagagct tatacagccg aatagcatta gcttgttatt ggatagcagt agatagatat  17817
ttctttataa tacttaggcg aattcatcac caaacgcctt gatgaacgaa cttgtctaac  17877
tgcttaccag aaaccaagca accaccaata accccagcac accgtgttca taacaatcag  17937
attcacaacc atcacgatga caccctggaa ccaccatagc ctcaacggga cgtatcccaa  17997
gttgaagaaa ggtggattgg tagagctggt gtagtgagtt aaatgcccag atagagttgt  18057
atacgcaagc gctctgcaac caagctccat cggaacacca gcggcctgca tgatctgcag  18117
gaacactggg aacatggcag agacatgtgc agtaatactt gcaaacagat actgggacac  18177
atagaaaata gccgtgcaaa tccatacact gccgtaagcc gccacacttg acaagtcgat  18237
cttttcggca aaccactcaa agaagccagt ttccttcaac tcagtagcca acatcagcaa  18297
cacaccgaac caaaggaaca aatcccaagc tccactgtta ttcac                  18342

<210> SEQ ID NO 2
<211> LENGTH: 510
<212> TYPE: PRT
<213> ORGANISM: Perkinsus marinus

<400> SEQUENCE: 2

Met Gln Val Pro Ala Glu His His Ser Thr Arg Val Ile Ser Ile Cys
1               5                   10                  15

Asp Ile Val Ile Ser Gly Pro Phe Gly Met Cys Asn His Asp Tyr Ser
            20                  25                  30

Ala Ser Ile Pro Ala Ser Ser Ser Gly Ser Thr Arg Arg Met Arg Leu
        35                  40                  45

Val Ala Tyr Ile Thr Leu Val Ser Ile His Tyr Gln Gln Leu Leu Phe
    50                  55                  60

Tyr Ser Ser Ile Ile Thr Ile Ile Thr Gly Tyr His Tyr Tyr Val Ala
65                  70                  75                  80

Ala Leu Pro Leu Tyr Asp Ile Ser Ile Ala Leu Ser Val Leu Ser Gly
```

-continued

```
                85                  90                  95
Leu Thr Leu Leu Trp Leu Cys Asn Cys Tyr Tyr Asn Ser Lys Pro Asn
                100                 105                 110

Val Phe Cys Ile Asp His Val Glu Phe Asp Ala Pro Pro Ser Trp Lys
            115                 120                 125

Val Ser His Glu Asp Ile Ile Asn Ile Ala Lys Ile Gln Gly Cys Tyr
        130                 135                 140

Thr Glu Asp Ser Leu Asn Phe Met Gln Arg Leu Leu Glu Arg Ser Gly
145                 150                 155                 160

Thr Cys Pro Asp Lys Ser Ala Ala Tyr Pro Pro Val Val Glu Ser
            165                 170                 175

Leu Arg Thr Asn Ala Pro Ala Asp Ala Ser Ala Val Asn Thr Arg Glu
                180                 185                 190

Glu Ala Arg Glu Val Ile Ile Thr Val Lys Asp Leu Leu Lys Lys
            195                 200                 205

Thr Gly Val His Pro Lys Ser Ile Asp Tyr Ile Val Asn Cys Ala
        210                 215                 220

Met Tyr Asn Pro Thr Pro Ser His Ala Ala Met Ile Val Asn Glu Val
225                 230                 235                 240

Gly Met Arg Asn Asp Val Ile Thr Tyr Asn Leu Ser Gly Met Gly Cys
                245                 250                 255

Ser Ala Gly Val Ile Thr Ile Asp Leu Ala Thr Arg Leu Leu Arg Glu
            260                 265                 270

Thr Arg Gly Arg Ala Leu Ile Val Ser Thr Glu Ile Leu Thr Arg Cys
        275                 280                 285

Phe Tyr Arg Gly Asn Asp Arg Glu Pro Leu Met Gly Asn Thr Leu Phe
        290                 295                 300

Arg Cys Gly Gly Ala Ala Ala Leu Leu Ser Ser Leu Pro Lys Asp Leu
305                 310                 315                 320

Ser Arg Ala Lys Tyr Lys Leu Leu His Thr Val Arg Thr Gln Val Leu
                325                 330                 335

Gly Asn Glu Ser Phe Glu Thr Ile Met Glu Thr Asp Asp Ser Thr Lys
            340                 345                 350

Pro Asn Ser Ile Val Thr Leu Arg Leu Gln Lys Ser Ile Ile Lys Val
            355                 360                 365

Ala Ala Val Ala Ile Lys Gln Asn Phe Thr Lys Leu Ala Tyr Met Val
        370                 375                 380

Leu Pro Leu Arg Glu Leu Leu Lys Val Leu Tyr Ser Met Val Thr Met
385                 390                 395                 400

Lys Met Arg Arg Lys Ser Ser Lys Glu Gly Arg Glu Leu Tyr Val Pro
                405                 410                 415

Asp Phe Arg Lys Gly Thr Asp His Trp Cys Ile His Ala Gly Gly Arg
            420                 425                 430

Gly Val Leu Asp Thr Leu Gln Asp Ser Leu Gln Leu Ser Asp Tyr Asp
        435                 440                 445

Ile Gln Ala Ser Arg Ser Val Leu Tyr Glu Arg Gly Asn Thr Ser Ser
    450                 455                 460

Ser Ser Ile Trp Tyr Glu Leu Ala Trp Leu Glu Arg Asp Gln Arg Ile
465                 470                 475                 480

Lys Arg Gly Asp Arg Val Leu Gln Leu Ala Phe Gly Ser Gly Phe Lys
                485                 490                 495

Cys Asn Ser Ser Val Trp Leu Ala Met His Asn Ile Asp Ala
            500                 505                 510
```

<210> SEQ ID NO 3
<211> LENGTH: 457
<212> TYPE: PRT
<213> ORGANISM: Perkinsus marinus

<400> SEQUENCE: 3

```
Met Thr Thr Ser Thr Thr Val Gln Leu Gln Glu Asp Leu Ser Ser
1               5                   10                  15

Gly Asp Gln Asn Ala His Pro Ser Pro Ser Arg Ala Thr Pro Ser Val
            20                  25                  30

Gly Asp Thr Lys Glu Asp Ala Arg Val Val Ile Lys Leu Phe Gly Thr
            35                  40                  45

Trp Val Asp Val Thr Ala Trp Leu Asn Asp His Pro Gly Gly Ser Lys
50                  55                  60

Val Leu Arg Ala Phe Asn Lys Lys Asp Ala Thr Asp Ala Val Met Ala
65                  70                  75                  80

Met His Thr Asp Glu Ala Ile Lys Arg Ile Ile Arg Phe Ser Asn Val
                85                  90                  95

Val Ser Ser Ala Pro Ile Asn Ala Ser Ile Gly Asp Val Gln Val Ile
            100                 105                 110

Glu Lys Ser Leu Ser Arg Glu Gln Leu Met Tyr Tyr Lys Leu Arg Thr
        115                 120                 125

Leu Ala Arg Asn Gln Gly Trp Phe Gln Ser Asn Leu Tyr Glu Gly
    130                 135                 140

Val Lys Ala Met Ile Ala Phe Gly Leu Leu Ile Ile Gly Phe Ala Thr
145                 150                 155                 160

Leu Tyr Phe Asp Tyr Gly Ile Trp Ser Thr Ala Leu Ile Gly Phe Ala
                165                 170                 175

Trp Phe Gln Leu Gly Trp Leu Gly His Asp Trp Ser His His Thr Ala
            180                 185                 190

Leu Pro Lys Ser Thr Thr Asn Cys Ala Asn Tyr Asn Asp Tyr Leu Gly
        195                 200                 205

Trp Leu Thr Gly Leu Ala Arg Gly Asn Thr Leu Leu Trp Trp Lys Leu
    210                 215                 220

Arg His Asn Thr His His Val Leu Thr Asn Gln Tyr Glu Asn Asp Pro
225                 230                 235                 240

Asp Ile Leu Thr Gln Pro Pro Leu His Phe Phe Glu Asp Phe Asp Val
                245                 250                 255

Gly Asn Val Asn Arg Tyr Gln Ala Val Tyr Tyr Leu Pro Met Leu Thr
            260                 265                 270

Leu Leu His Leu Phe Trp Leu Tyr Glu Ser Val Leu Val Cys Leu Arg
        275                 280                 285

Gln Ser Arg Ser Ile Asn Arg Tyr Asn Arg Met His Ala Arg Arg Asp
    290                 295                 300

Thr Val Ala Leu Val Leu His Ile Leu Ile Val Gly Ile Ile Ser Tyr
305                 310                 315                 320

Thr Ser Gly Lys Tyr Leu Leu Ile Leu Leu Ala Tyr Met Leu Ser Gly
                325                 330                 335

Phe Leu Thr Ala Val Val Val Phe Ala Ser His Tyr Asn Glu Pro Arg
            340                 345                 350

Val Ala Ser Gly Glu Ser Leu Ser Leu Val Arg Gln Thr Leu Leu Thr
        355                 360                 365

Thr Ile Asn Ile Gly Ser Phe Ser Asp Thr His Trp Glu Lys Lys Leu
    370                 375                 380
```

```
Trp Phe Tyr Leu Thr Gly Gly Leu Asn Met Gln Ile Glu His His Leu
385                 390                 395                 400

Phe Pro Thr Met Pro Arg His Asn Leu Pro Lys Thr Thr Phe Leu Val
                405                 410                 415

Lys Ser Leu Ala Gln Glu Leu Gly Leu Pro Tyr Lys Glu Thr Asn Ile
            420                 425                 430

Val Ser Leu Thr Lys Ala Ala Val Thr Thr Leu His His Asn Ala Leu
            435                 440                 445

Arg Asn Ile Glu Arg Leu Leu Ala Arg
        450                 455

<210> SEQ ID NO 4
<211> LENGTH: 411
<212> TYPE: PRT
<213> ORGANISM: Perkinsus marinus

<400> SEQUENCE: 4

Met Ser Ser Leu Thr Leu Tyr Arg Gly Pro Phe Ser Arg Met Val Leu
1               5                   10                  15

Pro Arg Gln Glu Ile Cys Ile Asn Gly Arg Ile Tyr Asp Val Thr Glu
                20                  25                  30

Phe Ile Asn Arg His Pro Gly Gly Lys Ile Ile Leu Phe Gln Val Gly
            35                  40                  45

Ala Asp Ala Thr Asp Ala Phe Arg Glu Phe His Ala Gly Ser Glu Lys
        50                  55                  60

Ala Glu Lys Ile Leu Lys Thr Leu Pro Ser Arg Asp Asp Asp Gly Thr
65                  70                  75                  80

Phe Leu Pro Ser Thr Gln Arg Ser Ile Met Asp Asp Phe Lys Arg Leu
                85                  90                  95

Arg Asp Asp Leu Val Ser Arg Gly Val Phe Lys Pro Ser Val Met His
            100                 105                 110

Val Val Tyr Arg Cys Leu Glu Val Ala Leu Tyr Leu Ile Gly Phe
            115                 120                 125

Tyr Leu Ala Leu Cys Thr Ser Asn Val Tyr Val Gly Cys Ala Val Leu
130                 135                 140

Gly Val Ala Gln Gly Arg Ala Gly Trp Leu Met His Glu Gly Gly His
145                 150                 155                 160

His Ser Leu Thr Gly Asn Trp Lys Val Asp Gln Phe Leu Gln Glu Leu
                165                 170                 175

Phe Phe Gly Ile Gly Cys Gly Met Ser Ala Ala Trp Trp Arg Asn Ala
            180                 185                 190

His Asn Lys His His Ala Ala Pro Gln His Leu Gly Lys Asp Val Asp
        195                 200                 205

Leu Glu Thr Leu Pro Leu Val Ala Phe Asn Lys Ala Val Leu Arg Gly
    210                 215                 220

Arg Leu Pro Ser Val Trp Ile Arg Ser Gln Ala Val Cys Phe Ala Pro
225                 230                 235                 240

Ile Ser Thr Leu Leu Val Ser Phe Phe Trp Gln Phe Tyr Leu His Pro
                245                 250                 255

Arg His Ile Ile Arg Thr Gly Arg Arg Met Glu Ser Phe Trp Leu Leu
            260                 265                 270

Val Arg Tyr Leu Val Ile Val Tyr Leu Gly Phe Ser Tyr Gly Leu Val
        275                 280                 285

Ser Val Leu Leu Cys Tyr Ile Ala Ser Val His Val Gly Gly Met Tyr
    290                 295                 300
```

Ile Phe Val His Phe Ala Leu Ser His Thr His Leu Pro Val Ile Asn
305                 310                 315                 320

Gln His Gly Arg Ala Asn Trp Leu Glu Tyr Ala Ser Lys His Thr Val
            325                 330                 335

Asn Val Ser Thr Asn Asn Tyr Phe Val Thr Trp Leu Met Ser Tyr Leu
        340                 345                 350

Asn Tyr Gln Ile Glu His His Leu Phe Pro Ser Cys Pro Gln Phe Arg
    355                 360                 365

Phe Pro Gly Tyr Val Ser Met Arg Val Arg Glu Phe Phe His Lys His
370                 375                 380

Gly Leu Lys Tyr Asn Glu Val Gly Tyr Leu His Ala Leu Asn Leu Thr
385                 390                 395                 400

Phe Ser Asn Leu Ala Ala Val Ala Ile Val Glu
            405                 410

<210> SEQ ID NO 5
<211> LENGTH: 27
<212> TYPE: DNA
<213> ORGANISM: Artificial Sequence
<220> FEATURE:
<223> OTHER INFORMATION: Primer sequence

<400> SEQUENCE: 5
atgcaagttc ccgcggagca tcactcc                                          27

<210> SEQ ID NO 6
<211> LENGTH: 31
<212> TYPE: DNA
<213> ORGANISM: Artificial Sequence
<220> FEATURE:
<223> OTHER INFORMATION: Primer sequence

<400> SEQUENCE: 6
cgttacgcat caatattatg catagccaac c                                     31

<210> SEQ ID NO 7
<211> LENGTH: 26
<212> TYPE: DNA
<213> ORGANISM: Artificial Sequence
<220> FEATURE:
<223> OTHER INFORMATION: Primer sequence with restriction sites for
      cloning into yeast expression vector

<400> SEQUENCE: 7
ttggtaccat gggatttcct gcggag                                           26

<210> SEQ ID NO 8
<211> LENGTH: 32
<212> TYPE: DNA
<213> ORGANISM: Artificial Sequence
<220> FEATURE:
<223> OTHER INFORMATION: Primer sequence

<400> SEQUENCE: 8
gggagctctt acgcatcaat attatgcata gc                                    32

<210> SEQ ID NO 9
<211> LENGTH: 1533
<212> TYPE: DNA
<213> ORGANISM: Perkinsus marinus
<220> FEATURE:
<221> NAME/KEY: CDS
<222> LOCATION: (1)

```
atg cga ttt cct gcg gag cgt cac ttc act cgg gtt ata tct atc tgt      48
Met Arg Phe Pro Ala Glu Arg His Phe Thr Arg Val Ile Ser Ile Cys
1               5                   10                  15 gat atc atc atc tca ggc ccc ttt gga atg tgt aac cat gat tac tcc      96
Asp Ile Ile Ile Ser Gly Pro Phe Gly Met Cys Asn His Asp Tyr Ser
            20                  25                  30 tct tct ata cct gcc tct tgt agt ggt agc act cga cgc atg cgt ttg     144
Ser Ser Ile Pro Ala Ser Cys Ser Gly Ser Thr Arg Arg Met Arg Leu
        35                  40                  45 gta gcc tac atc aca ttg gtc tct atc cac tat caa cag cta ctc ttt     192
Val Ala Tyr Ile Thr Leu Val Ser Ile His Tyr Gln Gln Leu Leu Phe
    50                  55                  60 tac tct tct atc gta act cta atc act ggc tat cac tac tat gtc gca     240
Tyr Ser Ser Ile Val Thr Leu Ile Thr Gly Tyr His Tyr Tyr Val Ala
65                  70                  75                  80 gct ctg ccc ctt tac gac ata tca ctt gct cta tct gtg ctt tcg gga     288
Ala Leu Pro Leu Tyr Asp Ile Ser Leu Ala Leu Ser Val Leu Ser Gly
                85                  90                  95 ata acg cta ctt tgg tta tgt aat tgc tat tac aac agc aag ccc aat     336
Ile Thr Leu Leu Trp Leu Cys Asn Cys Tyr Tyr Asn Ser Lys Pro Asn
            100                 105                 110 gta ttc tgc atc gat cat gct gag ttt gac gct ccc ccc tct tgg aag     384
Val Phe Cys Ile Asp His Ala Glu Phe Asp Ala Pro Pro Ser Trp Lys
        115                 120                 125 gtc agc cat gaa gac atc atc aac att gcc aag ata caa ggt tgc tac     432
Val Ser His Glu Asp Ile Ile Asn Ile Ala Lys Ile Gln Gly Cys Tyr
    130                 135                 140 acg gaa gat tca ctc aac ttc atg cag cgt ctt ctc gaa agg tct ggt     480
Thr Glu Asp Ser Leu Asn Phe Met Gln Arg Leu Leu Glu Arg Ser Gly
145                 150                 155                 160 act tgc cct ggt aag agt gct gct tac cct cca gtg gtt gtt gag tca     528
Thr Cys Pro Gly Lys Ser Ala Ala Tyr Pro Pro Val Val Val Glu Ser
                165                 170                 175 ttg agg act aac gcc ccc gct gat gcc tct gct gtc aat act aga gag     576
Leu Arg Thr Asn Ala Pro Ala Asp Ala Ser Ala Val Asn Thr Arg Glu
            180                 185                 190 gaa gcg agg gaa gtg atc ata act acg gtc aaa gat ctg ctt aag aag     624
Glu Ala Arg Glu Val Ile Ile Thr Thr Val Lys Asp Leu Leu Lys Lys
        195                 200                 205 act ggt gtg cat cct aaa tct att gac tat atc atc gtc aat tgc gcc     672
Thr Gly Val His Pro Lys Ser Ile Asp Tyr Ile Ile Val Asn Cys Ala
    210                 215                 220 atg tac aac ccg aca ccg tca cat gct gct atg ata gtg aat gaa gtc     720
Met Tyr Asn Pro Thr Pro Ser His Ala Ala Met Ile Val Asn Glu Val
225                 230                 235                 240 ggt atg agg aat gac gtc atc acc tat aac ctc agt ggt atg ggg tgt     768
Gly Met Arg Asn Asp Val Ile Thr Tyr Asn Leu Ser Gly Met Gly Cys
                245                 250                 255 agt gcc ggt gtt atc aca att gat cta gca acg cgt ctg ttg aga gag     816
Ser Ala Gly Val Ile Thr Ile Asp Leu Ala Thr Arg Leu Leu Arg Glu
            260                 265                 270 acc aga ggt agg gca ctg att gtg tca act gag ata cta act cgt tgc     864
Thr Arg Gly Arg Ala Leu Ile Val Ser Thr Glu Ile Leu Thr Arg Cys
        275                 280                 285 ttc tat cgt ggt aat gat cgt gaa cca ctg atg ggt aac aca tta ttc     912
Phe Tyr Arg Gly Asn Asp Arg Glu Pro Leu Met Gly Asn Thr Leu Phe
    290                 295                 300 aga tgt ggt ggt gct gct gct ttg cta tcg tca ttg cct aaa gac tta     960
Arg Cys Gly Gly Ala Ala Ala Leu Leu Ser Ser Leu Pro Lys Asp Leu
305                 310                 315                 320
```

-continued

| | |
|---|---|
| tct cgt ggt aaa tat aag ttg tta cat acc gta aga acg caa gtt ctc<br>Ser Arg Gly Lys Tyr Lys Leu Leu His Thr Val Arg Thr Gln Val Leu<br>                325                      330                      335 | 1008 |
| ggt aat gag agt ttt gaa acg att atg gag act gat gac agc acc aag<br>Gly Asn Glu Ser Phe Glu Thr Ile Met Glu Thr Asp Asp Ser Thr Lys<br>340                      345                      350 | 1056 |
| ccc aac agc att gtt aca ctc agg ctc cag aag agt att atc aaa gtt<br>Pro Asn Ser Ile Val Thr Leu Arg Leu Gln Lys Ser Ile Ile Lys Val<br>                355                      360                      365 | 1104 |
| gct gct gtt gct att aaa caa aat ttt act aag ctt gct tat gtg gtt<br>Ala Ala Val Ala Ile Lys Gln Asn Phe Thr Lys Leu Ala Tyr Val Val<br>370                      375                      380 | 1152 |
| ctg cct ctg aga gaa ctg ttg aag gtc gta tat tcg atg gtg atg atg<br>Leu Pro Leu Arg Glu Leu Leu Lys Val Val Tyr Ser Met Val Met Met<br>385                      390                      395                      400 | 1200 |
| aag atg agg agg aag tcg tca aaa gaa ggt cgt gag ttg tac gta cct<br>Lys Met Arg Arg Lys Ser Ser Lys Glu Gly Arg Glu Leu Tyr Val Pro<br>                405                      410                      415 | 1248 |
| gat ttt aga aag ggc att gat cat tgg tgt att cat gct ggt ggc cgt<br>Asp Phe Arg Lys Gly Ile Asp His Trp Cys Ile His Ala Gly Gly Arg<br>420                      425                      430 | 1296 |
| ggt gta ttg gat acc tta caa gat tct ctc cag cta tca gac tat gat<br>Gly Val Leu Asp Thr Leu Gln Asp Ser Leu Gln Leu Ser Asp Tyr Asp<br>435                      440                      445 | 1344 |
| atc caa gca agc cgt agt gtt ctt tat gag aga ggc aac acc agt agc<br>Ile Gln Ala Ser Arg Ser Val Leu Tyr Glu Arg Gly Asn Thr Ser Ser<br>                450                      455                      460 | 1392 |
| agt agc ata tgg tat gag ttg gca tgg ctc gaa cgt gac caa cgt att<br>Ser Ser Ile Trp Tyr Glu Leu Ala Trp Leu Glu Arg Asp Gln Arg Ile<br>465                      470                      475                      480 | 1440 |
| aag cgt gga gat agg gta tta cag gtg gct ttt ggt agt ggt ttc aaa<br>Lys Arg Gly Asp Arg Val Leu Gln Val Ala Phe Gly Ser Gly Phe Lys<br>                485                      490                      495 | 1488 |
| tgt aac tca tca gta tgg ttg gct atg cat aat att gat gcg taa<br>Cys Asn Ser Ser Val Trp Leu Ala Met His Asn Ile Asp Ala<br>500                      505                      510 | 1533 |

<210> SEQ ID NO 10
<211> LENGTH: 510
<212> TYPE: PRT
<213> ORGANISM: Perkinsus marinus
<220> FEATURE:

<400> SEQUENCE: 10

Met Arg Phe Pro Ala Glu Arg His Phe Thr Arg Val Ile Ser Ile Cys
1               5                   10                  15

Asp Ile Ile Ile Ser Gly Pro Phe Gly Met Cys Asn His Asp Tyr Ser
                20                  25                  30

Ser Ser Ile Pro Ala Ser Cys Ser Gly Ser Thr Arg Arg Met Arg Leu
            35                  40                  45

Val Ala Tyr Ile Thr Leu Val Ser Ile His Tyr Gln Gln Leu Leu Phe
        50                  55                  60

Tyr Ser Ser Ile Val Thr Leu Ile Thr Gly Tyr His Tyr Tyr Val Ala
65                  70                  75                  80

Ala Leu Pro Leu Tyr Asp Ile Ser Leu Ala Leu Ser Val Leu Ser Gly
                85                  90                  95

Ile Thr Leu Leu Trp Leu Cys Asn Cys Tyr Tyr Asn Ser Lys Pro Asn
            100                 105                 110

Val Phe Cys Ile Asp His Ala Glu Phe Asp Ala Pro Pro Ser Trp Lys

```
              115                 120                 125
Val Ser His Glu Asp Ile Ile Asn Ile Ala Lys Ile Gln Gly Cys Tyr
130                 135                 140

Thr Glu Asp Ser Leu Asn Phe Met Gln Arg Leu Leu Glu Arg Ser Gly
145                 150                 155                 160

Thr Cys Pro Gly Lys Ser Ala Ala Tyr Pro Pro Val Val Glu Ser
                165                 170             175

Leu Arg Thr Asn Ala Pro Ala Asp Ala Ser Ala Val Asn Thr Arg Glu
                180                 185                 190

Glu Ala Arg Glu Val Ile Ile Thr Thr Val Lys Asp Leu Leu Lys Lys
                195                 200                 205

Thr Gly Val His Pro Lys Ser Ile Asp Tyr Ile Ile Val Asn Cys Ala
210                 215                 220

Met Tyr Asn Pro Thr Pro Ser His Ala Ala Met Ile Val Asn Glu Val
225                 230                 235                 240

Gly Met Arg Asn Asp Val Ile Thr Tyr Asn Leu Ser Gly Met Gly Cys
                245                 250                 255

Ser Ala Gly Val Ile Thr Ile Asp Leu Ala Thr Arg Leu Leu Arg Glu
                260                 265                 270

Thr Arg Gly Arg Ala Leu Ile Val Ser Thr Glu Ile Leu Thr Arg Cys
275                 280                 285

Phe Tyr Arg Gly Asn Asp Arg Glu Pro Leu Met Gly Asn Thr Leu Phe
290                 295                 300

Arg Cys Gly Gly Ala Ala Ala Leu Leu Ser Ser Leu Pro Lys Asp Leu
305                 310                 315                 320

Ser Arg Gly Lys Tyr Lys Leu Leu His Thr Val Arg Thr Gln Val Leu
                325                 330                 335

Gly Asn Glu Ser Phe Glu Thr Ile Met Glu Thr Asp Ser Thr Lys
                340                 345                 350

Pro Asn Ser Ile Val Thr Leu Arg Leu Gln Lys Ser Ile Ile Lys Val
                355                 360                 365

Ala Ala Val Ala Ile Lys Gln Asn Phe Thr Lys Leu Ala Tyr Val Val
370                 375                 380

Leu Pro Leu Arg Glu Leu Leu Lys Val Val Tyr Ser Met Val Met Met
385                 390                 395                 400

Lys Met Arg Arg Lys Ser Ser Lys Glu Gly Arg Glu Leu Tyr Val Pro
                405                 410                 415

Asp Phe Arg Lys Gly Ile Asp Trp Cys Ile His Ala Gly Gly Arg
                420                 425                 430

Gly Val Leu Asp Thr Leu Gln Asp Ser Leu Gln Leu Ser Asp Tyr Asp
                435                 440                 445

Ile Gln Ala Ser Arg Ser Val Leu Tyr Glu Arg Gly Asn Thr Ser Ser
                450                 455                 460

Ser Ser Ile Trp Tyr Glu Leu Ala Trp Leu Glu Arg Asp Gln Arg Ile
465                 470                 475                 480

Lys Arg Gly Asp Arg Val Leu Gln Val Ala Phe Gly Ser Gly Phe Lys
                485                 490                 495

Cys Asn Ser Ser Val Trp Leu Ala Met His Asn Ile Asp Ala
                500                 505                 510

<210> SEQ ID NO 11
<211> LENGTH: 50
<212> TYPE: DNA
<213> ORGANISM: Artificial Sequence
<220> FEATURE:
```

```
<223> OTHER INFORMATION: Primer sequence

<400> SEQUENCE: 11
ggaattcgag gagtaggatc ttatctgagg atagtcacac tagtcgtact            50

<210> SEQ ID NO 12
<211> LENGTH: 25
<212> TYPE: DNA
<213> ORGANISM: Artificial Sequence
<220> FEATURE:
<223> OTHER INFORMATION: Primer sequence

<400> SEQUENCE: 12
catctgcgaa tactaaccat acatt                                       25
```